(12) United States Patent
Cheung-Flynn et al.

(10) Patent No.: US 11,149,064 B2
(45) Date of Patent: Oct. 19, 2021

(54) VASOACTIVE POLYPEPTIDES FOR SMOOTH MUSCLE RELAXATION

(71) Applicant: Vanderbilt University, Nashville, TN (US)

(72) Inventors: Joyce Cheung-Flynn, Nashville, TN (US); Colleen M Brophy, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 16/331,488

(22) PCT Filed: Sep. 7, 2017

(86) PCT No.: PCT/US2017/050550
§ 371 (c)(1),
(2) Date: Mar. 7, 2019

(87) PCT Pub. No.: WO2018/049071
PCT Pub. Date: Mar. 15, 2018

(65) Prior Publication Data
US 2019/0367559 A1  Dec. 5, 2019

Related U.S. Application Data

(60) Provisional application No. 62/384,629, filed on Sep. 7, 2016.

(51) Int. Cl.
| | | |
|---|---|---|
| C07K 7/08 | (2006.01) | |
| C07K 14/47 | (2006.01) | |
| A61K 38/00 | (2006.01) | |

(52) U.S. Cl.
CPC ............ *C07K 7/08* (2013.01); *C07K 14/4703* (2013.01); *A61K 38/00* (2013.01); *C07K 2319/10* (2013.01)

(58) Field of Classification Search
None
See application file for complete search history.

(56) References Cited

U.S. PATENT DOCUMENTS

| | | | | |
|---|---|---|---|---|
| 4,891,358 A | * | 1/1990 | DiMaio ...................... | A61P 3/00 514/9.7 |
| 2003/0060399 A1 | | 3/2003 | Brophy et al. | |
| 2009/0170165 A1 | | 7/2009 | Lee et al. | |
| 2009/0258819 A1 | | 10/2009 | Brophy et al. | |
| 2010/0075377 A1 | | 3/2010 | West et al. | |

FOREIGN PATENT DOCUMENTS

| | | | |
|---|---|---|---|
| WO | WO99/24473 A | 5/1999 | |
| WO | WO2010/040024 A2 | 4/2010 | |
| WO | WO-2011072292 A2 * | 6/2011 | ............ G01N 33/68 |

OTHER PUBLICATIONS

Alcock et al., "Science Progress in the Twentieth Century: A Quarterly Journal of Scientific Thought, vol. 2", 1907, p. 108 (Year: 1907).*
Gillett et al., GenBank: CAA64685.1—cofilin [*Homo sapiens*]; 1996. (Year: 1196).*
Gunst et al.,"Actin cytoskeletal dynamics in smooth muscle: a new paradigm for the regulation of smooth muscle contraction", American Journal of Physiology Cell Physiology, 2008, p. C576-C587 (Year: 2008).*
UniProtKB—P23528 (COF1_HUMAN), 2018, pp. 1-9 (Year: 2018).*
Hora et al., GenBank: AGF32894.1; 2013 (Year: 2013).*
Smith et al., Yperthermia-triggered intracellular delivery of anti-cancer agent to HER2+ cells by HER2-specific affibody (ZHER2-GS-Cys)-conjugated thermosensitive liposomes (HER2+ affisomes), Journal of Controlled Release, 2011, pp. 187-194 (Year: 2011).*
Fischer et al., Sustained relief of neuropathic pain by AAV-targets expression of CBD3 peptide in rat dorsal root ganglion, Gene Therapy, 2014, pp. 44-51 (Year: 2014).*
Alcock et al., Science Progress in the Twentieth Century: A Quarterly Journal of Scientific Thought, vol. II, 1907, p. 108 (Year: 1907).*
Wieske et al., "Defined sequence segments of the small heat shock proteins HSP25 and aB crystallin inhibit actin polymerization", Eur. J. Biochem., 2001, 2083-2090 (Year: 2001).*
Butt et al: 11 cAMP- and cGMP-dependent protein kinase phosphorylation sites of the focal adhesion vasodilator-stimulated phosphoprotein (VASP) in vitro and in intact human platelets, Journal of Biological Chemistry, American Society for Biochemistry and Molecular Biology, US, vol. 269, No. 20, May 20, 1994 (May 20, 1994), pp. 14509-14517.

* cited by examiner

*Primary Examiner* — Lianko G Garyu
(74) *Attorney, Agent, or Firm* — Stites & Harbison PLLC; Sean P. Ritchie

(57) ABSTRACT

A polypeptide, a pharmaceutical composition including a polypeptide, and a method for treating a condition using a polypeptide are provided. The polypeptide includes an amino acid sequence according to the general formula X1-X2-X3, wherein X1 and X3 are independently absent or comprise a transduction domain, X2 includes Z3, and Z3 is selected from the group consisting of serine or phosphoserine analogs. The pharmaceutical composition includes a polypeptide including an amino acid sequence according to the general formula X1-X2-X3 and one or more components selected from the group consisting of a pharmaceutically acceptable carrier, a calcium channel blocker, and a combination thereof. X1 and X3 are independently absent or comprise a transduction domain, X2 includes Z3, and Z3 is selected from the group consisting of serine or phosphoserine analogs. The method of treating a condition includes administering a polypeptide including an amino acid sequence according to the general formula X1-X2-X3 to a subject in need thereof, wherein X1 and X3 are independently absent or comprise a transduction domain, X2 includes Z3, and Z3 is selected from the group consisting of serine or phosphoserine analogs. Also provided is a biomedical device including a polypeptide.

17 Claims, 9 Drawing Sheets

Specification includes a Sequence Listing.

| SEQ ID NO. | Peptides | Sequences | Composition | | |
|---|---|---|---|---|---|
| | | | X1 | X2 | X3 |
| 1 | Cofi1 | YARAAARQARAA(pS)GVAVSDG | YARAAARQARA | A(pS)GVAVSDG | |
| 2 | Cofi3 | YARAAARQARAA(pS)GVTVSDEVI | YARAAARQARA | A(pS)GVTVSDEVI | |
| 3 | APi | YARAAARQARAIRQTADRWRVSLDVN | YARAAARQARA | IRQTADRWRVSLDVN | |
| 4 | APi2 | IRQTADRWRVSLDVNLTVK | | IRQTADRWRVSLDVN | LTVK |
| 5 | VASP1 | YARAAARQARAKLRKV(pS)K | YARAAARQARA | KLRV(pS)K | |
| 6 | VASP2 | YARAAARQARAKLRKV(pS)KQEEA | YARAAARQARA | KLRV(pS)KQEEA | |
| 7 | VASP3 | YARAAARQARAKLRKV(pS)KQEEASG | YARAAARQARA | KLRV(pS)KQEEASG | |
| 8 | VASP1.2 | KLRKV(pS)KLTVK | | KLRKVSK | LTVK |
| 9 | VASP1.3 | KLRKV(pS)K | | KLRKVSK | |
| 10 | scrVASP1 | YARAAARQARAK(pS)RVLKK | YARAAARQARA | K(pS)RVLKK | |
| 11 | PalmVASP | YARAAARQARA{K(palm)}LRKV(pS)K | YARAAARQARA | {K(palm)}LRKV(pS)K | |
| 12 | MidPalmVASP | YARAARQARA{K(palm)}GGKLRKV(pS)K | YARAAARQARA | {K(palm)}GGKLRKV(pS)K | |

Figure 1

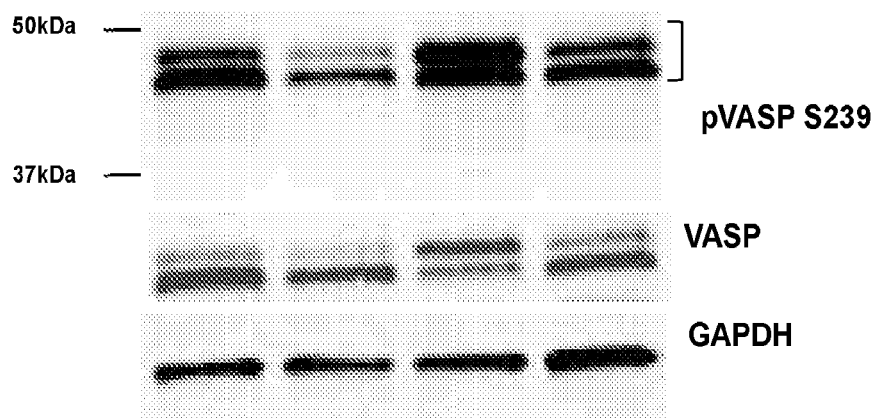
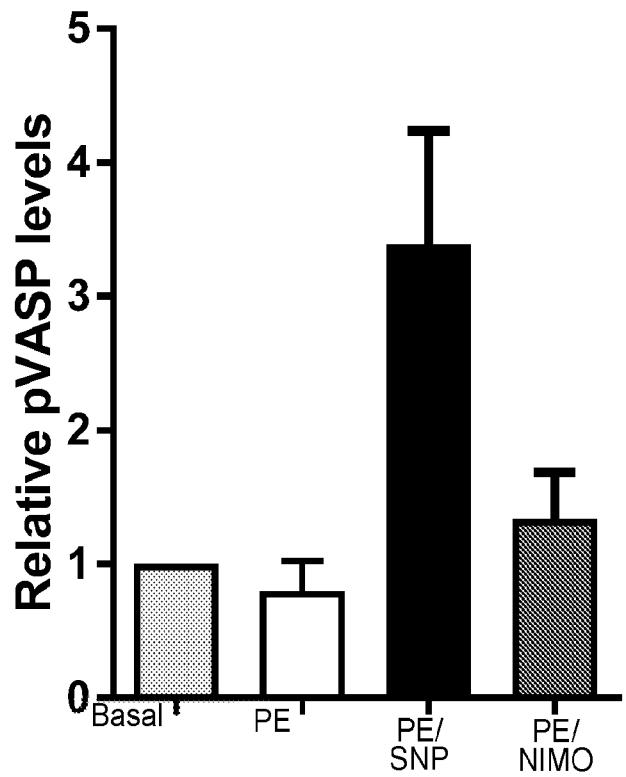
Figure 3A

SEQUENCE LISTING

```
<160> NUMBER OF SEQ ID NOS: 43

<210> SEQ ID NO 1
<211> LENGTH: 20
<212> TYPE: PRT
<213> ORGANISM: Artificial
<220> FEATURE:
<223> OTHER INFORMATION: Synthetic polypeptide
<220> FEATURE:
<221> NAME/KEY: PHOSPHORYLATION
<222> LOCATION: (13)..(13)

<400> SEQUENCE: 1

Tyr Ala Arg Ala Ala Ala Arg Gln Ala Arg Ala Ala Ser Gly Val Ala
1               5                   10                  15

Val Ser Asp Gly
            20

<210> SEQ ID NO 2
<211> LENGTH: 22
<212> TYPE: PRT
<213> ORGANISM: Artificial
<220> FEATURE:
<223> OTHER INFORMATION: Synthetic polypeptide
```

```
<220> FEATURE:
<221> NAME/KEY: PHOSPHORYLATION
<222> LOCATION: (13)..(13)

<400> SEQUENCE: 2

Tyr Ala Arg Ala Ala Ala Arg Gln Ala Arg Ala Ala Ser Gly Val Thr
1               5                   10                  15

Val Ser Asp Glu Val Ile
            20

<210> SEQ ID NO 3
<211> LENGTH: 26
<212> TYPE: PRT
<213> ORGANISM: Artificial
<220> FEATURE:
<223> OTHER INFORMATION: Synthetic polypeptide

<400> SEQUENCE: 3

Tyr Ala Arg Ala Ala Ala Arg Gln Ala Arg Ala Ile Arg Gln Thr Ala
1               5                   10                  15

Asp Arg Trp Arg Val Ser Leu Asp Val Asn
            20                  25

<210> SEQ ID NO 4
<211> LENGTH: 19
<212> TYPE: PRT
<213> ORGANISM: Artificial
<220> FEATURE:
<223> OTHER INFORMATION: Synthetic polypeptide

<400> SEQUENCE: 4

Ile Arg Gln Thr Ala Asp Arg Trp Arg Val Ser Leu Asp Val Asn Leu
1               5                   10                  15

Thr Val Lys

<210> SEQ ID NO 5
<211> LENGTH: 18
<212> TYPE: PRT
<213> ORGANISM: Artificial
<220> FEATURE:
<223> OTHER INFORMATION: Synthetic polypeptide
<220> FEATURE:
<221> NAME/KEY: PHOSPHORYLATION
<222> LOCATION: (17)..(17)

<400> SEQUENCE: 5

Tyr Ala Arg Ala Ala Ala Arg Gln Ala Arg Ala Lys Leu Arg Lys Val
1               5                   10                  15

Ser Lys

<210> SEQ ID NO 6
<211> LENGTH: 22
<212> TYPE: PRT
<213> ORGANISM: Artificial
<220> FEATURE:
<223> OTHER INFORMATION: Synthetic polypeptide
<220> FEATURE:
<221> NAME/KEY: PHOSPHORYLATION
<222> LOCATION: (17)..(17)

<400> SEQUENCE: 6

Tyr Ala Arg Ala Ala Ala Arg Gln Ala Arg Ala Lys Leu Arg Lys Val
1               5                   10                  15

Ser Lys Gln Glu Glu Ala
            20
```

<210> SEQ ID NO 7
<211> LENGTH: 24
<212> TYPE: PRT
<213> ORGANISM: Artificial
<220> FEATURE:
<223> OTHER INFORMATION: Synthetic polypeptide
<220> FEATURE:
<221> NAME/KEY: PHOSPHORYLATION
<222> LOCATION: (17)..(17)

<400> SEQUENCE: 7

Tyr Ala Arg Ala Ala Ala Arg Gln Ala Arg Ala Lys Leu Arg Lys Val
1               5                   10                  15

Ser Lys Gln Glu Glu Ala Ser Gly
            20

<210> SEQ ID NO 8
<211> LENGTH: 11
<212> TYPE: PRT
<213> ORGANISM: Artificial
<220> FEATURE:
<223> OTHER INFORMATION: Synthetic polypeptide
<220> FEATURE:
<221> NAME/KEY: PHOSPHORYLATION
<222> LOCATION: (6)..(6)

<400> SEQUENCE: 8

Lys Leu Arg Lys Val Ser Lys Leu Thr Val Lys
1               5                   10

<210> SEQ ID NO 9
<211> LENGTH: 7
<212> TYPE: PRT
<213> ORGANISM: Artificial
<220> FEATURE:
<223> OTHER INFORMATION: Synthetic polypeptide
<220> FEATURE:
<221> NAME/KEY: PHOSPHORYLATION
<222> LOCATION: (6)..(6)

<400> SEQUENCE: 9

Lys Leu Arg Lys Val Ser Lys
1               5

<210> SEQ ID NO 10
<211> LENGTH: 18
<212> TYPE: PRT
<213> ORGANISM: Artificial
<220> FEATURE:
<223> OTHER INFORMATION: Synthetic polypeptide
<220> FEATURE:
<221> NAME/KEY: PHOSPHORYLATION
<222> LOCATION: (13)..(13)

<400> SEQUENCE: 10

Tyr Ala Arg Ala Ala Ala Arg Gln Ala Arg Ala Lys Ser Arg Val Leu
1               5                   10                  15

Lys Lys

<210> SEQ ID NO 11
<211> LENGTH: 18
<212> TYPE: PRT
<213> ORGANISM: Artificial
<220> FEATURE:
<223> OTHER INFORMATION: Synthetic polypeptide
<220> FEATURE:
<221> NAME/KEY: BINDING

```
<222> LOCATION: (12)..(12)
<223> OTHER INFORMATION: Palmitic acid conjugation
<220> FEATURE:
<221> NAME/KEY: PHOSPHORYLATION
<222> LOCATION: (17)..(17)

<400> SEQUENCE: 11

Tyr Ala Arg Ala Ala Ala Arg Gln Ala Arg Ala Lys Leu Arg Lys Val
1               5                   10                  15

Ser Lys

<210> SEQ ID NO 12
<211> LENGTH: 21
<212> TYPE: PRT
<213> ORGANISM: Artificial
<220> FEATURE:
<223> OTHER INFORMATION: Synthetic polypeptide
<220> FEATURE:
<221> NAME/KEY: BINDING
<222> LOCATION: (12)..(12)
<223> OTHER INFORMATION: Palmitic acid conjugation
<220> FEATURE:
<221> NAME/KEY: PHOSPHORYLATION
<222> LOCATION: (20)..(20)

<400> SEQUENCE: 12

Tyr Ala Arg Ala Ala Ala Arg Gln Ala Arg Ala Lys Gly Gly Lys Leu
1               5                   10                  15

Arg Lys Val Ser Lys
            20

<210> SEQ ID NO 13
<211> LENGTH: 13
<212> TYPE: PRT
<213> ORGANISM: Artificial
<220> FEATURE:
<223> OTHER INFORMATION: Synthetic peptide

<400> SEQUENCE: 13

Gly Arg Lys Lys Arg Arg Gln Arg Arg Arg Pro Pro Gln
1               5                   10

<210> SEQ ID NO 14
<211> LENGTH: 12
<212> TYPE: PRT
<213> ORGANISM: Artificial
<220> FEATURE:
<223> OTHER INFORMATION: Synthetic peptide

<400> SEQUENCE: 14

Ala Tyr Ala Arg Ala Ala Ala Arg Gln Ala Arg Ala
1               5                   10

<210> SEQ ID NO 15
<211> LENGTH: 34
<212> TYPE: PRT
<213> ORGANISM: Artificial
<220> FEATURE:
<223> OTHER INFORMATION: Synthetic peptide

<400> SEQUENCE: 15

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu
```

<210> SEQ ID NO 16
<211> LENGTH: 27
<212> TYPE: PRT
<213> ORGANISM: Artificial
<220> FEATURE:
<223> OTHER INFORMATION: Synthetic peptide

<400> SEQUENCE: 16

Gly Trp Thr Leu Asn Ser Ala Gly Tyr Leu Leu Gly Leu Ile Asn Leu
1               5                   10                  15

Lys Ala Leu Ala Ala Leu Ala Lys Lys Ile Leu
            20                  25

<210> SEQ ID NO 17
<211> LENGTH: 11
<212> TYPE: PRT
<213> ORGANISM: Artificial
<220> FEATURE:
<223> OTHER INFORMATION: Synthetic peptide

<400> SEQUENCE: 17

Pro Leu Ser Ser Ile Ser Arg Ile Gly Asp Pro
1               5                   10

<210> SEQ ID NO 18
<211> LENGTH: 16
<212> TYPE: PRT
<213> ORGANISM: Artificial
<220> FEATURE:
<223> OTHER INFORMATION: Synthetic peptide

<400> SEQUENCE: 18

Ala Ala Val Ala Leu Leu Pro Ala Val Leu Leu Ala Leu Leu Ala Pro
1               5                   10                  15

<210> SEQ ID NO 19
<211> LENGTH: 12
<212> TYPE: PRT
<213> ORGANISM: Artificial
<220> FEATURE:
<223> OTHER INFORMATION: Synthetic peptide

<400> SEQUENCE: 19

Ala Ala Val Leu Leu Pro Val Leu Leu Ala Ala Pro
1               5                   10

<210> SEQ ID NO 20
<211> LENGTH: 15
<212> TYPE: PRT
<213> ORGANISM: Artificial
<220> FEATURE:
<223> OTHER INFORMATION: Synthetic peptide

<400> SEQUENCE: 20

Val Thr Val Leu Ala Leu Gly Ala Leu Ala Gly Val Gly Val Gly
1               5                   10                  15

<210> SEQ ID NO 21
<211> LENGTH: 21
<212> TYPE: PRT
<213> ORGANISM: Artificial
<220> FEATURE:
<223> OTHER INFORMATION: Synthetic peptide

<400> SEQUENCE: 21

Gly Ala Leu Phe Leu Gly Trp Leu Gly Ala Ala Gly Ser Thr Met Gly
1               5                   10                  15

Ala Trp Ser Gln Pro
            20

<210> SEQ ID NO 22
<211> LENGTH: 27
<212> TYPE: PRT
<213> ORGANISM: Artificial
<220> FEATURE:
<223> OTHER INFORMATION: Synthetic peptide

<400> SEQUENCE: 22

Gly Trp Thr Leu Asn Ser Ala Gly Tyr Leu Leu Gly Leu Ile Asn Leu
1               5                   10                  15

Lys Ala Leu Ala Ala Leu Ala Lys Lys Ile Leu
            20                  25

<210> SEQ ID NO 23
<211> LENGTH: 18
<212> TYPE: PRT
<213> ORGANISM: Artificial
<220> FEATURE:
<223> OTHER INFORMATION: Synthetic peptide

<400> SEQUENCE: 23

Lys Leu Ala Leu Lys Leu Ala Leu Lys Ala Leu Lys Ala Ala Leu Lys
1               5                   10                  15

Leu Ala

<210> SEQ ID NO 24
<211> LENGTH: 21
<212> TYPE: PRT
<213> ORGANISM: Artificial
<220> FEATURE:
<223> OTHER INFORMATION: Synthetic peptide

<400> SEQUENCE: 24

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 25
<211> LENGTH: 16
<212> TYPE: PRT
<213> ORGANISM: Artificial
<220> FEATURE:
<223> OTHER INFORMATION: Synthetic peptide

<400> SEQUENCE: 25

Lys Ala Phe Ala Lys Leu Ala Ala Arg Leu Tyr Arg Lys Ala Gly Cys
1               5                   10                  15

<210> SEQ ID NO 26
<211> LENGTH: 16
<212> TYPE: PRT
<213> ORGANISM: Artificial
<220> FEATURE:
<223> OTHER INFORMATION: Synthetic peptide

```
<400> SEQUENCE: 26

Lys Ala Phe Ala Lys Leu Ala Ala Arg Leu Tyr Arg Ala Ala Gly Cys
1               5                   10                  15

<210> SEQ ID NO 27
<211> LENGTH: 16
<212> TYPE: PRT
<213> ORGANISM: Artificial
<220> FEATURE:
<223> OTHER INFORMATION: Synthetic peptide

<400> SEQUENCE: 27

Ala Ala Phe Ala Lys Leu Ala Ala Arg Leu Tyr Arg Lys Ala Gly Cys
1               5                   10                  15

<210> SEQ ID NO 28
<211> LENGTH: 16
<212> TYPE: PRT
<213> ORGANISM: Artificial
<220> FEATURE:
<223> OTHER INFORMATION: Synthetic peptide

<400> SEQUENCE: 28

Lys Ala Phe Ala Ala Leu Ala Ala Arg Leu Tyr Arg Lys Ala Gly Cys
1               5                   10                  15

<210> SEQ ID NO 29
<211> LENGTH: 16
<212> TYPE: PRT
<213> ORGANISM: Artificial
<220> FEATURE:
<223> OTHER INFORMATION: Synthetic peptide

<400> SEQUENCE: 29

Lys Ala Phe Ala Lys Leu Ala Ala Gln Leu Tyr Arg Lys Ala Gly Cys
1               5                   10                  15

<210> SEQ ID NO 30
<211> LENGTH: 16
<212> TYPE: PRT
<213> ORGANISM: Artificial
<220> FEATURE:
<223> OTHER INFORMATION: Synthetic peptide

<400> SEQUENCE: 30

Ala Gly Gly Gly Gly Tyr Gly Arg Lys Lys Arg Arg Gln Arg Arg Arg
1               5                   10                  15

<210> SEQ ID NO 31
<211> LENGTH: 11
<212> TYPE: PRT
<213> ORGANISM: Artificial
<220> FEATURE:
<223> OTHER INFORMATION: Synthetic peptide

<400> SEQUENCE: 31

Tyr Gly Arg Lys Lys Arg Arg Gln Arg Arg Arg
1               5                   10

<210> SEQ ID NO 32
<211> LENGTH: 11
<212> TYPE: PRT
<213> ORGANISM: Artificial
<220> FEATURE:
<223> OTHER INFORMATION: Synthetic peptide
```

```
<400> SEQUENCE: 32

Tyr Ala Arg Ala Ala Arg Gln Ala Arg Ala
1               5                   10

<210> SEQ ID NO 33
<211> LENGTH: 4
<212> TYPE: PRT
<213> ORGANISM: Artificial
<220> FEATURE:
<223> OTHER INFORMATION: Synthetic peptide

<400> SEQUENCE: 33

Leu Thr Val Lys
1

<210> SEQ ID NO 34
<211> LENGTH: 15
<212> TYPE: PRT
<213> ORGANISM: Artificial
<220> FEATURE:
<223> OTHER INFORMATION: Synthetic peptide

<400> SEQUENCE: 34

Ile Arg Gln Thr Ala Asp Arg Trp Arg Val Ser Leu Asp Val Asn
1               5                   10                  15

<210> SEQ ID NO 35
<211> LENGTH: 9
<212> TYPE: PRT
<213> ORGANISM: Artificial
<220> FEATURE:
<223> OTHER INFORMATION: Synthetic peptide
<220> FEATURE:
<221> NAME/KEY: PHOSPHORYLATION
<222> LOCATION: (2)..(2)

<400> SEQUENCE: 35

Ala Ser Gly Val Ala Val Ser Asp Gly
1               5

<210> SEQ ID NO 36
<211> LENGTH: 11
<212> TYPE: PRT
<213> ORGANISM: Artificial
<220> FEATURE:
<223> OTHER INFORMATION: Synthetic peptide
<220> FEATURE:
<221> NAME/KEY: PHOSPHORYLATION
<222> LOCATION: (2)..(2)

<400> SEQUENCE: 36

Ala Ser Gly Val Thr Val Ser Asp Glu Val Ile
1               5                   10

<210> SEQ ID NO 37
<211> LENGTH: 7
<212> TYPE: PRT
<213> ORGANISM: Artificial
<220> FEATURE:
<223> OTHER INFORMATION: Synthetic peptide
<220> FEATURE:
<221> NAME/KEY: PHOSPHORYLATION
<222> LOCATION: (6)..(6)

<400> SEQUENCE: 37

Lys Leu Arg Lys Val Ser Lys
1               5
```

<210> SEQ ID NO 38
<211> LENGTH: 11
<212> TYPE: PRT
<213> ORGANISM: Artificial
<220> FEATURE:
<223> OTHER INFORMATION: Synthetic peptide
<220> FEATURE:
<221> NAME/KEY: PHOSPHORYLATION
<222> LOCATION: (6)..(6)

<400> SEQUENCE: 38

Lys Leu Arg Lys Val Ser Lys Gln Glu Glu Ala
1               5                   10

<210> SEQ ID NO 39
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: PHOSPHORYLATION
<222> LOCATION: (6)..(6)

<400> SEQUENCE: 39

Lys Leu Arg Lys Val Ser Lys Gln Glu Glu Ala Ser Gly
1               5                   10

<210> SEQ ID NO 40
<211> LENGTH: 6
<212> TYPE: PRT
<213> ORGANISM: Artificial
<220> FEATURE:
<223> OTHER INFORMATION: Synthetic peptide
<220> FEATURE:
<221> NAME/KEY: PHOSPHORYLATION
<222> LOCATION: (5)..(5)

<400> SEQUENCE: 40

Lys Leu Arg Val Ser Lys
1               5

<210> SEQ ID NO 41
<211> LENGTH: 7
<212> TYPE: PRT
<213> ORGANISM: Artificial
<220> FEATURE:
<223> OTHER INFORMATION: Synthetic peptide
<220> FEATURE:
<221> NAME/KEY: PHOSPHORYLATION
<222> LOCATION: (2)..(2)

<400> SEQUENCE: 41

Lys Ser Arg Val Leu Lys Lys
1               5

<210> SEQ ID NO 42
<211> LENGTH: 7
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (1)..(1)
<223> OTHER INFORMATION: Palmitic acid conjugation
<220> FEATURE:
<221> NAME/KEY: PHOSPHORYLATION
<222> LOCATION: (6)..(6)

```
<400> SEQUENCE: 42

Lys Leu Arg Lys Val Ser Lys
1               5

<210> SEQ ID NO 43
<211> LENGTH: 10
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (1)..(1)
<223> OTHER INFORMATION: Palmitic acid conjugation
<220> FEATURE:
<221> NAME/KEY: PHOSPHORYLATION
<222> LOCATION: (9)..(9)

<400> SEQUENCE: 43

Lys Gly Gly Lys Leu Arg Lys Val Ser Lys
1               5                   10
```

VASOACTIVE POLYPEPTIDES FOR SMOOTH MUSCLE RELAXATION

RELATED APPLICATIONS

This application claims priority from International Patent Application No. PCT/US2017/050550, filed Sep. 7, 2017, which claims the benefit of U.S. Provisional Application Ser. No. 62/384,629, filed Sep. 7, 2016, the entire disclosures of which are incorporated herein by this reference.

GOVERNMENT INTEREST

This invention was made with government support under grant numbers R01HL070715, R01HL105731, and UL1 TR000445-06 awarded by the National Institute of Health (NIH). The government has certain rights in the invention.

SEQUENCE LISTING

This application contains a Sequence Listing which has been submitted in ASCII format via EFS-Web and is hereby incorporated by reference in its entirety. The ASCII copy of the Sequence Listing, which was created on Sep. 7, 2017, is named 11672N-17029W.txt and is 12 kilobytes in size.

TECHNICAL FIELD

The presently-disclosed subject matter generally relates to peptides, compositions including peptides, and methods for use thereof. More specifically, the presently-disclosed subject matter relates to smooth muscle relaxing polypeptides, pharmaceutical compositions including smooth muscle relaxing polypeptides, and methods of using such polypeptides and pharmaceutical compositions.

BACKGROUND

Smooth muscles are found in the walls of blood vessels, airways, the gastrointestinal tract, and the genitourinary tract. Pathologic tonic contraction of smooth muscle constitutes spasm. Many pathological conditions are associated with spasm of vascular smooth muscle ("vasospasm"), the smooth muscle that lines blood vessels. For example, hypertension (high blood pressure) is caused by excessive vasoconstriction, as well as thickening, of the vessel wall, particularly in the smaller vessels of the circulation. Additionally, vasospasm can cause symptoms such as angina and ischemia (if a heart artery is involved), or stroke as in the case of subarachnoid hemorrhage (SAH)-induced vasospasm if a brain vessel is involved.

Therapeutic options to prevent vasospasm and its sequelae represent a large, unmet need. Often, therapies directed towards SAH-induced vasospasm do not improve patient outcomes. Additionally, these medications may cause systemic hypotension, an undesirable side effect, by lacking specificity for cerebral-selective vasodilator responses.

Accordingly, there remains a need for methods and products that provide effective smooth muscle relaxation without the undesirable side effects associated with existing therapies.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter is directed, in some embodiments, to a polypeptide comprising an amino acid sequence according to the general formula X1-X2-X3, wherein X1 and X3 are independently absent or comprise a transduction domain, wherein X2 includes Z3, and wherein Z3 is selected from the group consisting of serine or phosphoserine analogs. In one embodiment, the polypeptide is a smooth muscle relaxing polypeptide. In one embodiment, X2 is selected from the group consisting of IRQTADRWRVSLDVN (SEQ ID NO: 34), A(pS)GVAVSDG (SEQ ID NO: 35), A(pS)GVTVSDEVI (SEQ ID NO: 36), KLRV(pS)K (SEQ ID NO: 37), KLRV(pS)KQEEA (SEQ ID NO: 38), KLRV(pS)KQEEASG (SEQ ID NO: 39), KLRKV(pS)K (SEQ ID NO: 40), K(pS)RVLKK (SEQ ID NO: 41), {K(palm)}LRKV(pS)K (SEQ ID NO: 42), {K(palm)}GGKLRKV(pS)K (SEQ ID NO: 43), and a combination thereof; and wherein pS is a phosphoserine analog. In another embodiment, X1 and X3 are selected from the group consisting of GRKKRRQRRRPPQ (SEQ ID NO: 13), AYARAAARQARA (SEQ ID NO: 14), DAATATRGRSAASRPTERPRAPARSASRPRRPVE (SEQ ID NO: 15), GWTLNSAGYLLGLINLKALAALAKKIL (SEQ ID NO: 16), PLSSISRIGDP (SEQ ID NO: 17), AAVALLPAVLLALLAP (SEQ ID NO: 18), AAVLLPVLLAAP (SEQ ID NO: 19), VTVLALGALAGVGVG (SEQ ID NO: 20), GALFLGWLGAAGSTMGAWSQP (SEQ ID NO: 21), GWTLNSAGYLLGLINLKALAALAKKIL (SEQ ID NO: 22), KLALKLALKALKAALKLA (SEQ ID NO: 23), KETWWETWWTEWSQPKKKRKV (SEQ ID NO: 24), KAFAKLAARLYRKAGC (SEQ ID NO: 25), KAFAKLAARLYRAAGC (SEQ ID NO: 26), AAFAKLAARLYRKAGC (SEQ ID NO: 27), KAFAALAARLYRKAGC (SEQ ID NO: 28), KAFAKLAAQLYRKAGC (SEQ ID NO: 29), AGGGGYGRKKRRQRRR (SEQ ID NO: 30), YGRKKRRQRRR (SEQ ID NO: 31), YARAAARQARA (SEQ ID NO: 32), LTVK (SEQ ID NO: 33), and combinations thereof. In a further embodiment, the polypeptide includes a sequence selected from the group consisting of YARAAARQARAA(pS)GVAVSDG (SEQ ID NO: 1), YARAAARQARAA(pS)GVTVSDEVI (SEQ ID NO: 2), YARAAARQARAIRQTADRWRVSLDVN (SEQ ID NO: 3), IRQTADRWRVSLDVNLTVK (SEQ ID NO: 4), YARAAARQARAKLRV(pS)K (SEQ ID NO: 5), YARAAARQARAKLRV(pS)KQEEA (SEQ ID NO: 6), YARAAARQARAKLRV(pS)KQEEASG (SEQ ID NO: 7), KLRKV(pS)KLTVK (SEQ ID NO: 8), YARAAARQARA{K(palm)}LRKV(pS)K (SEQ ID NO: 11), YARAAARQARA{K(palm)}GGKLRKV(pS)K (SEQ ID NO: 12), and combinations thereof wherein (pS) denotes a phosphoserine analog and {K(palm)} denotes palmitic acid conjugated lysine.

In some embodiments, the polypeptide further comprising one or more mimics of a phosphorylated amino acid residue. In one embodiment, the amino acid residue is selected from the group consisting of D, E, and combinations thereof.

In some embodiments, the polypeptide includes one or more formulation modifications. In one embodiment, the one or more formulation modifications are selected from the group consisting of polymeric nanoparticles, lipidic nanoparticles, drug-polymer conjugates, and combinations thereof. In some embodiments, the polypeptide includes one or more chemical modifications. In one embodiment, the chemical modifications are selected from the group consisting of incorporation of non-natural amino acids, glycosylation, PEGylation, lipidation, cyclization, and combinations thereof. In some embodiments, the polypeptide is modified with at least one molecule having one or more aromatic rings. In one embodiment, the one or more aromatic rings are independently substituted with at least one substituent selected from the group consisting of halogen, lower alkyl, lower alkylthio, trifluoromethyl, lower acyloxy, aryl, heteroaryl, and combinations thereof. In another embodiment, the at least one molecule includes 9-fluorenylmethyl. In a further embodiment, the at least one molecule is selected from the group consisting of 9-fluorenylmethylcarbonyl, 9-fluorenylmethylcarbamates, 9-fluorenylmethylcarbonates, 9-fluorenylmethyl esters, 9-fluorenylmethylphosphates, S-9-fluorenylmethyl thioethers, or a combination thereof.

Also provided herein, in some embodiments, is a pharmaceutical composition comprising a polypeptide including an amino acid sequence according to the general formula X1-X2-X3 and one or more components selected from the group consisting of a pharmaceutically acceptable carrier, a calcium channel blocker, and a combination thereof. X1 and X3 are independently absent or comprise a transduction domain, X2 includes Z3, and Z3 is selected from the group consisting of serine or phosphoserine analogs. In one embodiment, the calcium block is selected from the group consisting of nifedipine and nimodipine.

Further provided herein, in some embodiments, is a method of treating a condition, the method comprising administering a polypeptide including an amino acid sequence according to the general formula X1-X2-X3 to a subject in need thereof, wherein X1 and X3 are independently absent or comprise a transduction domain, X2 includes Z3, and Z3 is selected from the group consisting of serine or phosphoserine analogs. In one embodiment, administering the polypeptide is for a therapeutic use selected from the group consisting of (a) promoting smooth muscle relaxation and preventing vasospasm; (b) neuroprotection (c) regulating actin polymerization; (d) platelet aggregation; (e) treating or inhibiting one or more of subarachnoid induced vasospasm, intimal hyperplasia, stenosis, restenosis, atherosclerosis, smooth muscle spasm, angina, Prinzmetal's angina (coronary vasospasm), ischemia, stroke, hypertension, pulmonary (lung) hypertension, asthma (bronchospasm), Raynaud's disease or phenomenon, non-occlusive mesenteric ischemia, anal fissure, achalasia, sexual dysfunction, migraine, vasculopathy, such as transplant vasculopathy, stunned myocardium, pulmonary hypertension, and gastrointestinal motility disorders. In another embodiment, the therapeutic use is for subarachnoid hemorrhaging. In a further embodiment, the therapeutic use is for asthma.

Still further provided herein, in some embodiments, is a biomedical device biomedical devices comprising one or more polypeptide including an amino acid sequence according to the general formula X1-X2-X3, wherein X1 and X3 are independently absent or comprise a transduction domain, X2 includes Z3, and Z3 is selected from the group consisting of serine or phosphoserine analogs. In one embodiment, the polypeptide is disposed on the biomedical device. In another embodiment, the polypeptide is disposed in the biomedical device. In a further embodiment, the polypeptide is disposed on and in the biomedical device. In some embodiments, the one or more polypeptides are phosphorylated. In some embodiments, the biomedical device include stents, grafts, shunts, stent grafts, angioplasty devices, balloon catheters, fistulas, wound dressings, any implantable drug delivery device, or a combination thereof.

BRIEF DESCRIPTION OF THE DRAWINGS

The novel features of the subject matter of the present disclosure are set forth with particularity in the appended claims. A better understanding of the features and advantages of the presently disclosed subject matter will be obtained by reference to the following detailed description that sets forth illustrative embodiments, in which the principles of the present disclosure are used, and the accompanying drawings of which:

FIG. 1 shows a table listing example sequences of smooth muscle relaxing polypeptide compositions according to the general formula I:X1-X2-X3. Sequences of polypeptides indicated by single-letter amino acid code. (pS) denotes phosphoserine. {K(palm)} denotes palmitic acid conjugated lysine.

FIGS. 3A-B show graphs and images of an immunoblot illustrating that vasorelaxation is associated with phosphorylation of the VASP protein. Rat aorta rings, denuded of endothelium, were cut and suspended a muscle bath. After equilibration, tissues were untreated (Basal) or pre-contract with 50 uM phenylephrine (PE) followed by 100 nM sodium nitroprusside (SNP) or 1 µM nimodipine (NIMO). Tissues were snap-frozen under tension (arrows). (A) Proteins were extracted from the tissues and immunoblotted for phosphorylation with the antibodies (Ab) indicated. A mobility shift from 46 kDa to 50 kDa is caused by phosphorylation. (B) Representative muscle bath tracings.

BRIEF DESCRIPTION OF THE SEQUENCE LISTING

Figure 2:
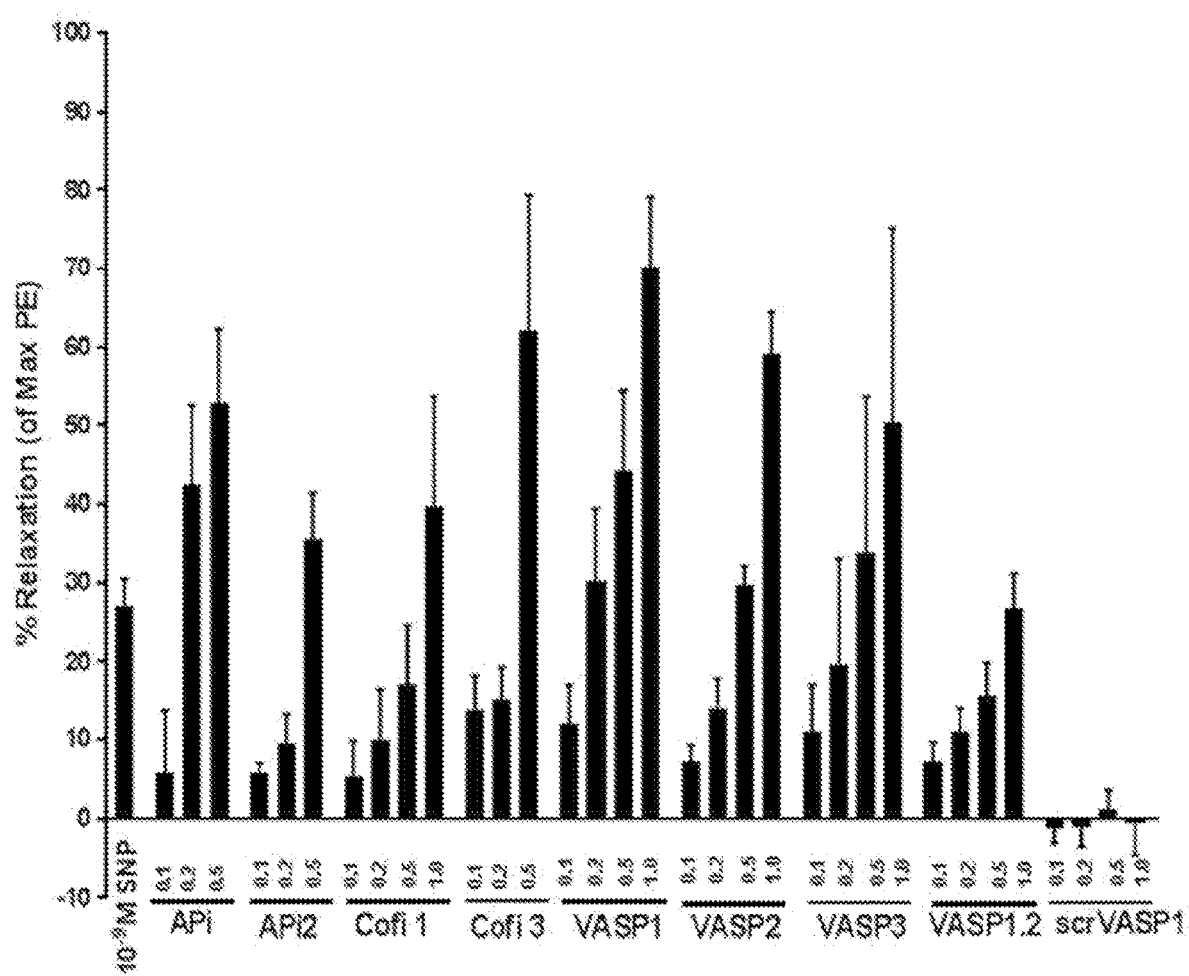
FIG. 2 shows a graph illustrating the vasorelaxation effects of polypeptides. Freshly isolated rat aorta denuded of endothelium were suspended in a muscle bath and force generated were recorded. Phenylephrine-precontracted tissues were treated with either sodium nitroprusside (1 nM) or escalating doses of the polypeptides indicated (0.1 to 1.0 mM). Contractile response was defined by stress, which was calculated using the force generated by the tissues. [$10^5$ Newtons (N)/$m^2$]–force (g)×0.0987/area, where area is equal to the wet weight [(mg)/length (mm at maximal length)] divided by 1.055). Percent relaxation were determined as a change to the maximal phenylephrine-induced contraction. Data are reported as mean responses±standard error of the mean. n=3-17.

SEQ ID NO: 1 is an amino acid sequence for a phosphopeptide analogue of cofilin.
SEQ ID NO: 2 is an amino acid sequence for a phosphopeptide analogue of cofilin.
SEQ ID NO: 3 is an amino acid sequence for a peptide analogue of HSP27.
SEQ ID NO: 4 is an amino acid sequence for a peptide analogue of HSP27.
SEQ ID NO: 5 is an amino acid sequence for a phosphopeptide analogue of VASP.
SEQ ID NO: 6 is an amino acid sequence for a phosphopeptide analogue of VASP.
SEQ ID NO: 7 is an amino acid sequence for a phosphopeptide analogue of VASP.
SEQ ID NO: 8 is an amino acid sequence for a phosphopeptide analogue of VASP.
SEQ ID NO: 9 is an amino acid sequence for a control peptide
SEQ ID NO: 10 is an amino acid sequence for a control peptide.
SEQ ID NO: 11 is an amino acid sequence for PalmVASP.
SEQ ID NO: 12 is an amino acid sequence for Mid-PalmVASP.
SEQ ID NO: 13 is an amino acid sequence for a transduction domain.
SEQ ID NO: 14 is an amino acid sequence for a transduction domain.
SEQ ID NO: 15 is an amino acid sequence for a transduction domain.
SEQ ID NO: 16 is an amino acid sequence for a transduction domain.
SEQ ID NO: 17 is an amino acid sequence for a transduction domain.
SEQ ID NO: 18 is an amino acid sequence for a transduction domain.
SEQ ID NO: 19 is an amino acid sequence for a transduction domain.
SEQ ID NO: 20 is an amino acid sequence for a transduction domain.

SEQ ID NO: 21 is an amino acid sequence for a transduction domain.

SEQ ID NO: 22 is an amino acid sequence for a transduction domain.

SEQ ID NO: 23 is an amino acid sequence for a transduction domain.

SEQ ID NO: 24 is an amino acid sequence for a transduction domain.

SEQ ID NO: 25 is an amino acid sequence for a transduction domain.

SEQ ID NO: 26 is an amino acid sequence for a transduction domain.

SEQ ID NO: 27 is an amino acid sequence for a transduction domain.

SEQ ID NO: 28 is an amino acid sequence for a transduction domain.

SEQ ID NO: 29 is an amino acid sequence for a transduction domain.

SEQ ID NO: 30 is an amino acid sequence for a transduction domain.

SEQ ID NO: 31 is an amino acid sequence for a transduction domain.

SEQ ID NO: 32 is an amino acid sequence for a transduction domain.

SEQ ID NO: 33 is an amino acid sequence for a transduction domain.

SEQ ID NO: 34 is an amino acid sequence for an X2 domain.

SEQ ID NO: 35 is an amino acid sequence for an X2 domain.

SEQ ID NO: 36 is an amino acid sequence for an X2 domain.

SEQ ID NO: 37 is an amino acid sequence for an X2 domain.

SEQ ID NO: 38 is an amino acid sequence for an X2 domain.

SEQ ID NO: 39 is an amino acid sequence for an X2 domain.

SEQ ID NO: 40 is an amino acid sequence for an X2 domain.

SEQ ID NO: 41 is an amino acid sequence for an X2 domain.

SEQ ID NO: 42 is an amino acid sequence for an X2 domain.

SEQ ID NO: 43 is an amino acid sequence for an X2 domain.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732). For example, the single letter designation for amino acids is used predominately herein. As is well known by one of skill in the art, such single letter designations are as follows: A is alanine; C is cysteine; D is aspartic acid; E is glutamic acid; F is phenylalanine; G is glycine; H is histidine; I is isoleucine; K is lysine; L is leucine; M is methionine; N is asparagine; P is proline; Q is glutamine; R is arginine; S is serine; T is threonine; V is valine; W is tryptophan; and Y is tyrosine.

Although any methods, devices, and materials similar or equivalent to those described herein can be used in the practice or testing of the presently-disclosed subject matter, representative methods, devices, and materials are described herein.

Following long-standing patent law convention, the terms "a", "an", and "the" refer to "one or more" when used in this application, including the claims, unless the context clearly dictates otherwise. Thus, for example, reference to "a polypeptide" includes one or more of such polypeptides, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, a "biomedical device" refers to a device to be implanted into a subject, for example, a human being, in order to bring about a desired result. Particularly preferred biomedical devices according to this aspect of the invention include, but are not limited to, stents, grafts, shunts, stent grafts, fistulas, angioplasty devices, balloon catheters, endovascular coiling, implantable drug delivery devices, wound dressings such as films (e.g., polyurethane films), hydrocolloids (hydrophilic colloidal particles bound to polyurethane foam), hydrogels (cross-linked polymers containing about at least 60% water), foams (hydrophilic or hydrophobic), calcium alginates (nonwoven composites of fibers from calcium alginate), cellophane, and biological polymers.

As used herein, the term "grafts" refers to both natural and prosthetic grafts and implants. In a most preferred embodiment, the graft is a vascular graft.

As used herein, the term "stent" includes the stent itself, as well as any sleeve or other component that may be used to facilitate stent placement.

As used herein, "disposed on or in" means that the one or more polypeptides can be either directly or indirectly in contact with an outer surface, an inner surface, or embedded within the biomedical device. "Direct" contact refers to disposition of the polypeptides directly on or in the device, including but not limited to soaking a biomedical device in a solution containing the one or more polypeptides, spin coating or spraying a solution containing the one or more polypeptides onto the device, implanting any device that would deliver the polypeptide, and administering the polypeptide through a catheter directly on to the surface or into any organ.

As used herein, "indirect" contact means that the one or more polypeptides do not directly contact the biomedical device. For example, the one or more polypeptides may be disposed in a matrix, such as a gel matrix or a viscous fluid, which is disposed on the biomedical device. Such matrices can be prepared to, for example, modify the binding and release properties of the one or more polypeptides as required.

As used herein, "treat" or "treating" means accomplishing one or more of the following: (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

As used herein, the term "inhibit" or "inhibiting" means to limit the disorder in individuals at risk of developing the disorder.

As used herein, "administering" includes in vivo administration, as well as administration directly to tissue ex vivo, such as vein grafts.

The presently-disclosed subject matter includes peptides, compositions including the peptides, and methods for use thereof. In some embodiments, the peptides include a polypeptide. The term "polypeptide" is used in its broadest sense to refer to a sequence of subunit amino acids, amino acid analogs, or peptidomimetics. In one embodiment, the subunits are linked by peptide bonds. In another embodiment, the polypeptides can have peptidomimetic bonds, such as ester bonds, to prepare peptides with novel properties. For example, a peptide may be generated that incorporates a reduced peptide bond, i.e., R.sub.1-CH.sub.2-NH—R.sub.2, where R.sub.1 and R.sub.2 are amino acid residues or sequences. A reduced peptide bond may be introduced as a dipeptide subunit. Such a polypeptide would be resistant to protease activity, and would possess an extended half-live in vivo.

In some embodiments, the polypeptides are of a sequence according to the general formula I: X1-X2-X3. In formula I, X1 and X3 are independently absent or comprise a transduction domain. In one embodiment, at least one of X1 and X3 comprises a transduction domain. In another embodiment, both X1 and X3 comprise transduction domains. As used herein, the term "transduction domain" is interchangeably referred to as a "cell permeant peptide domain," and means one or more amino acid sequence or any other molecule that can carry the active domain across cell membranes. Suitable transduction domain(s) include, but are not limited to, GRKKRRQRRRPPQ (SEQ ID NO: 13); AYARAAARQARA (SEQ ID NO: 14); DAATATRGRSAASRPTERPRAPARSASRPRRPVE (SEQ ID NO: 15); GWTLNSAGYLLGLINLKALAALAKKIL (SEQ ID NO: 16); PLSSISRIGDP (SEQ ID NO: 17); AAVALLPAVLLALLAP (SEQ ID NO: 18); AAVLLPVLLAAP (SEQ ID NO: 19); VTVLALGALAGVGVG (SEQ ID NO: 20); GALFLGWLGAAGSTMGAWSQP (SEQ ID NO: 21); GWTLNSAGYLLGLINLKALAALAKKIL (SEQ ID NO: 22); KLALKLALKALKAALKLA (SEQ ID NO: 23); KETWWETWWTEWSQPKKKRKV (SEQ ID NO: 24); KAFAKLAARLYRKAGC (SEQ ID NO: 25); KAFAKLAARLYRAAGC (SEQ ID NO: 26); AAFAKLAARLYRKAGC (SEQ ID NO: 27); KAFAALAARLYRKAGC (SEQ ID NO: 28); KAFAKLAAQLYRKAGC (SEQ ID NO: 29), AGGGGYGRKKRRQRRR (SEQ ID NO: 30); YGRKKRRQRRR (SEQ ID NO: 31); YARAAARQARA (SEQ ID NO: 32); and LTVK (SEQ ID NO: 33).

The transduction domains can be linked to other polypeptides to direct movement of the linked polypeptide across cell membranes. In some embodiments, the transducing molecules do not need to be covalently linked to the active polypeptide. For example, in certain embodiments, the transduction domain is linked to the rest of the polypeptide, such as the X2 domain, via peptide bonding. (See, e.g., Cell 55: 1179-1188, 1988; Cell 55: 1189-1193, 1988; Proc Natl Acad Sci USA 91: 664-668, 1994; Science 285: 1569-1572, 1999; J Biol Chem. 276: 3254-3261, 2001; and Cancer Res 61: 474-477, 2001)

The X2 domain is the active domain. In some embodiments, the X2 domain is or forms a vasodilating sequence and/or peptide. In one embodiment, X2 contains Z3, which is selected from the group consisting of serine, phosphoserine, or palmitic acid conjugated lysine analogs. That is, in one embodiment, the X2 domain includes at least one amino acid selected from the group consisting of serine, phosphoserine, or palmitic acid conjugated lysine analogs. In another embodiment, for example, X2 includes IRQTADRWRVSLDVN (SEQ ID NO: 34), A(pS)GVAVSDG (SEQ ID NO: 35), A(pS)GVTVSDEVI (SEQ ID NO: 36), KLRKV(pS)K (SEQ ID NO: 37), KLRKV(pS)KQEEA (SEQ ID NO: 38), KLRKV(pS)KQEEASG (SEQ ID NO: 39), KLRV(pS)K (SEQ ID NO: 40), K(pS)RVLKK (SEQ ID NO: 41), {K(palm)}LRKV(pS)K (SEQ ID NO: 42), {K(palm)}GGKLRKV(pS)K (SEQ ID NO: 43), or a combination thereof, where (pS) is phosphoserine analogs (also referred to herein as "phosphoserine mimics") and {K(palm)} is palmitic acid conjugated lysine. In a further embodiment, any S residue may be replaced by a pS residue and/or any pS residue may be replaced by a S residue. Suitable phosphoserine mimics include, but are not limited to, sulfoserine, amino acid mimics containing a methylene substitution for the phosphate oxygen, 4-phosphono(difluoromethyl)phenylanaline, and L-2-amino-4-(phosphono)-4,4-difuorobutanoic acid. Other phosphoserine mimics can be made by those of skill in the art; for example, see Otaka et al., Tetrahedron Letters 36: 927-930 (1995). Additionally or alternatively, the polypeptides disclosed herein may include one or more other mimic of a phosphorylated amino acid residue, such as D and/or E.

To form the polypeptides of formula I, any one of the X2 domains disclosed herein may be combined with any one or more of the transduction domains disclosed herein. For example, SEQ ID NO: 34 may be combined with any one or more of SEQ ID NOs: 13-33, SEQ ID NO: 35 may be combined with any one or more of SEQ ID NOs: 13-33, SEQ ID NO: 36 may be combined with any one or more of SEQ ID NOs: 13-33, SEQ ID NO: 37 may be combined with any one or more of SEQ ID NOs: 13-33, SEQ ID NO: 38 may be combined with any one or more of SEQ ID NOs: 13-33, SEQ ID NO: 39 may be combined with any one or more of SEQ ID NOs: 13-33, SEQ ID NO: 40 may be combined with any one or more of SEQ ID NOs: 13-33, SEQ ID NO: 41 may be combined with any one or more of SEQ ID NOs: 13-33, SEQ ID NO: 42 may be combined with any one or more of SEQ ID NOs: 13-33, and/or SEQ ID NO: 43 may be combined with any one or more of SEQ ID NOs: 13-33. Each individual combination above is explicitly disclosed and contemplated herein.

In certain embodiments, any one of the X2 domains may be combined with any one of the X1 or X3 transduction domains disclosed herein. Such peptides include, but are not limited to, YARAAARQARAA(pS)GVAVSDG (SEQ ID NO: 1), YARAAARQARAA(pS)GVTVSDEVI (SEQ ID NO: 2), YARAAARQARAIRQTADRWRVSLDVN (SEQ ID NO: 3), IRQTADRWRVSLDVNLTVK (SEQ ID NO: 4), YARAAARQARAKLRKV(pS)K (SEQ ID NO: 5), YARAAARQARAKLRKV(pS)KQEEA (SEQ ID NO: 6), YARAAARQARAKLRKV(pS)KQEEASG (SEQ ID NO: 7), KLRKV(pS)KLTVK (SEQ ID NO: 8), KLRKV(pS)K (SEQ ID NO: 9), YARAAARQARAK(pS)RVLKK (SEQ ID NO: 10), YARAAARQARA{K(palm)}LRKV(pS)K (SEQ ID NO: 11), and/or YARAAARQARA{K(palm)}GGKLRKV(pS)K (SEQ ID NO: 12) (FIG. 1, TABLE 1).

TABLE 1

Smooth Muscle Relaxing Polypeptides According to Formula I

| SEQ ID NO. | Peptide | X1 | X2 | Sequence X3 |
|---|---|---|---|---|
| 1 | Cofi1 | YARAAARQARA | A(pS)GVAVSDG | |
| 2 | Cofi3 | YARAAARQARA | A(pS)GVTVSDEVI | |
| 3 | APi | YARAAARQARA | IRQTADRWRVSLDVN | |
| 4 | APi2 | | IRQTADRWRVSLDVN | LTVK |
| 5 | VASP1 | YARAAARQARA | KLRKV(pS)K | |
| 6 | VASP2 | YARAAARQARA | KLRKV(pS)KQEEA | |
| 7 | VASP3 | YARAAARQARA | KLRKV(pS)KQEEASG | |
| 8 | VASP1.2 | | KLRKV(pS)K | LTVK |
| 9 | VASP1.3 | | KLRKV(pS)K | |
| 10 | scrVASP1 | YARAAARQARA | K(pS)RVLKK | |
| 11 | PalmVASP | YARAAARQARA | {K(palm)}LRKV(pS)K | |
| 12 | MidPalmVASP | YARAAARQARA | {K(palm)}GGKLRKV(pS)K | |

Sequences indicated by single-letter amino acid code. (pS) denotes phosphoserine; {K(palm)} denotes palmitic acid conjugated lysine.

Figure 3B:
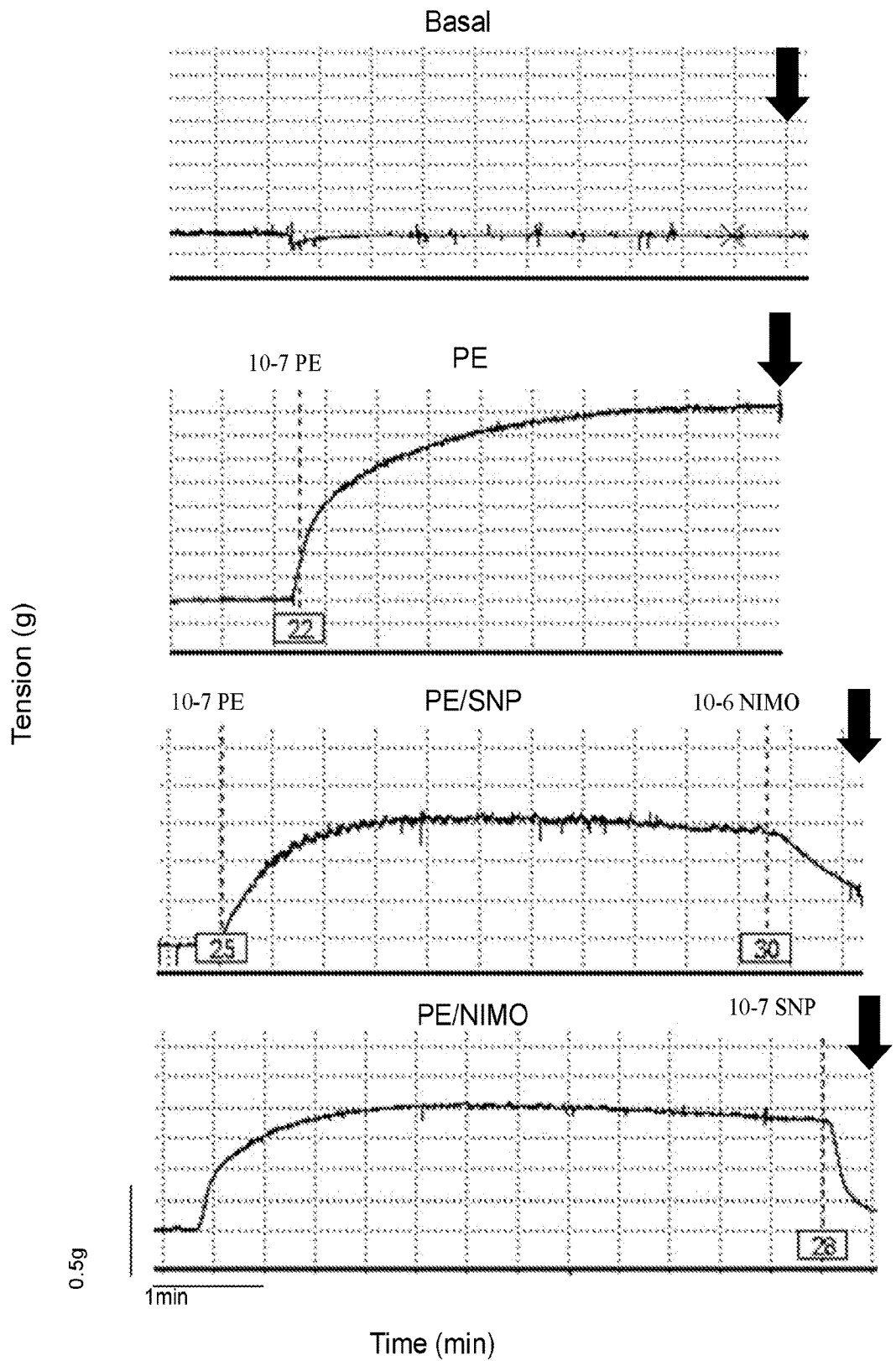
Figure 4A:
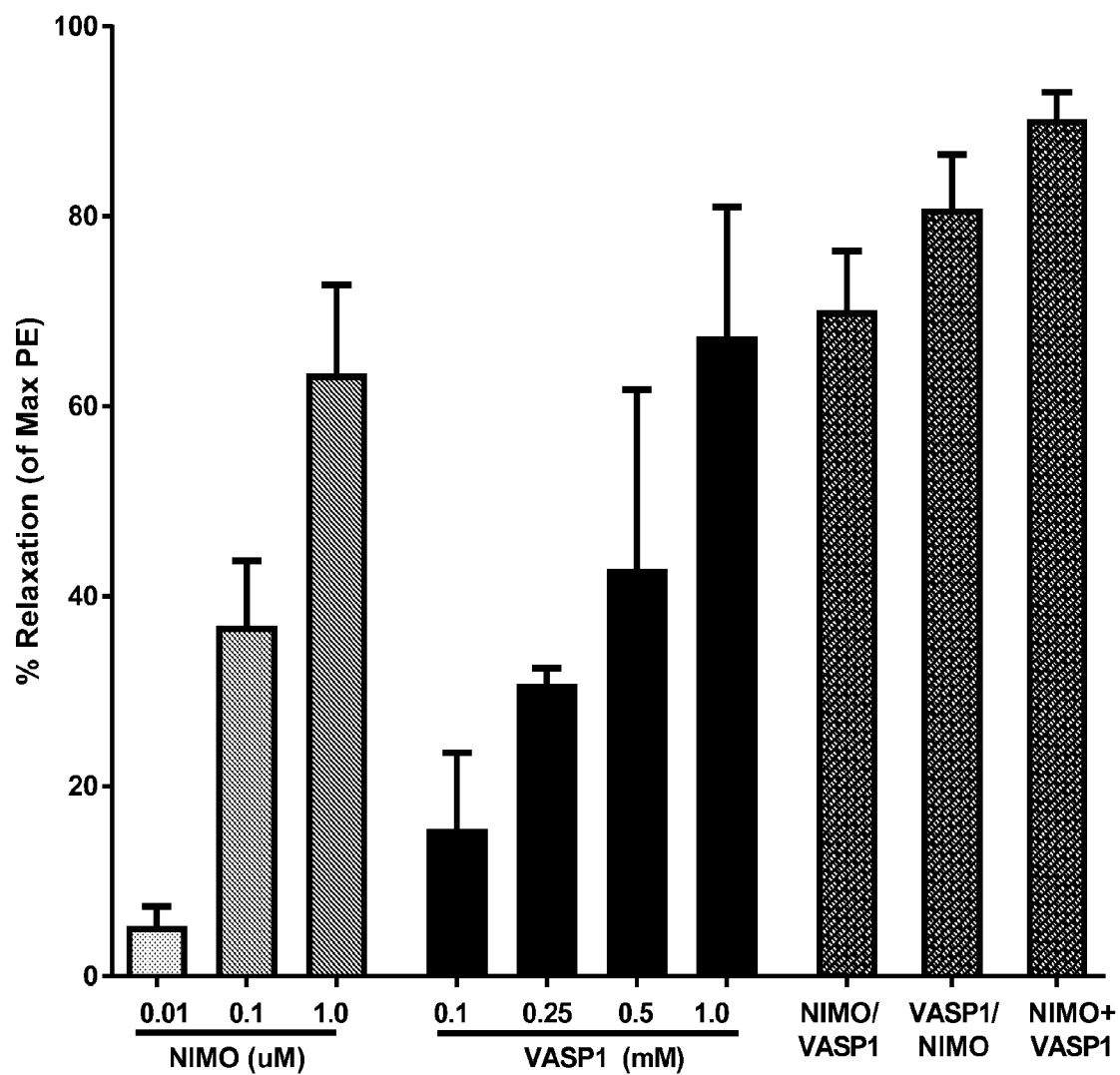
FIGS. 4A and B show graphs illustrating the effects of nimodipine on polypeptide induced vasorelaxation in phenylephrine precontracted rat aortic smooth muscle. Freshly isolated rat aorta denuded of endothelium were suspended in a muscle bath and force generated were recorded. Phenylephrine-precontracted tissues were treated either with escalating doses of the calcium channel blocker nimodipine (NIMO; 0.01 to 1 uM), the VASP1 polypeptide (0.1 to 1.0 mM), nimodipine (0.1 µM) followed by the VASP1 polypeptide (0.25 mM) [NIMO/VASP1], the VASP1 polypeptide (0.25 mM) followed by nimodipine (0.1 µM) [VASP1/NIMO], or simultaneous addition of nimodipine (0.1 µM) plus the VASP1 polypeptide (0.25 mM) [NIMO+VASP1]. Contractile response was defined by stress, which was calculated using the force generated by the tissues. [$10^5$ Newtons (N)/$m^2$]=force (g)×0.0987/area, where area is equal to the wet weight [(mg)/length (mm at maximal length)] divided by 1.055). (A) Percent relaxation were determined as a change to the maximal phenylephrine-induced contraction. Data are reported as mean responses±standard error of the mean. n=3-4. (B). Representative tracings of force generated in response to phenylephrine, nimodipine and the VASP1 polypeptides.
Figure 4B:
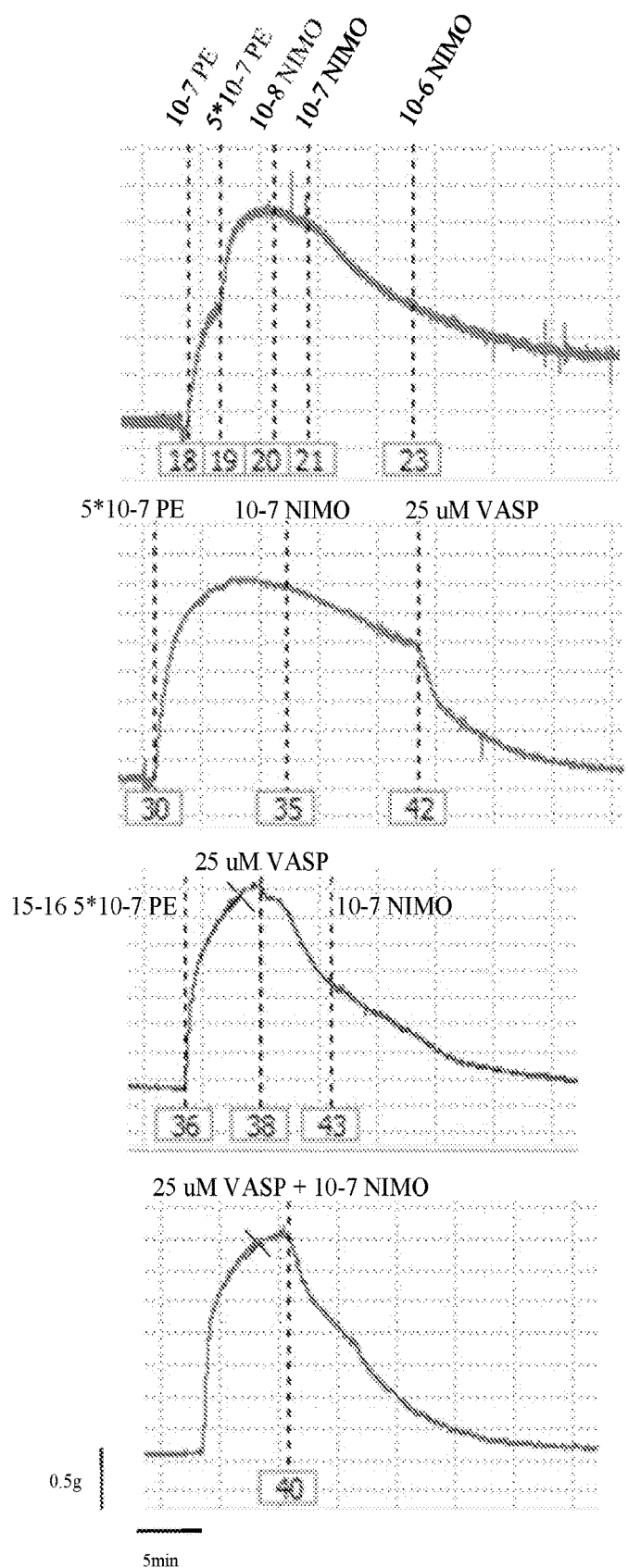
Figure 6:
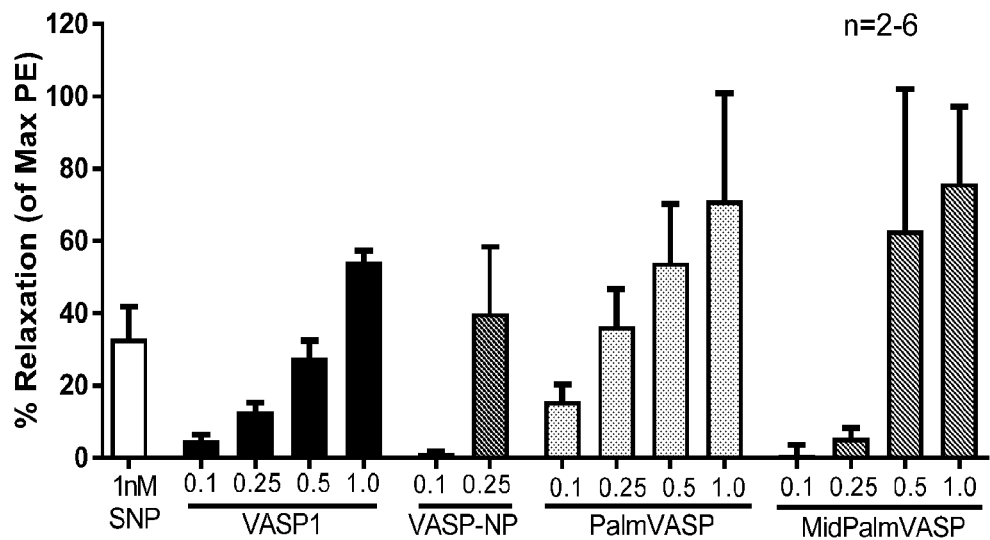
FIG. 6 shows a graph illustrating the effects of chemical and formulatory modification on potency of VASP on phenylephrine-precontracted rat aortic smooth muscle relaxation. Freshly isolated rat aorta denuded of endothelium were suspended in a muscle bath, and force generated were recorded. Phenylephrine-precontracted tissues were treated with either sodium nitroprusside (1 nM) or escalating doses of the polypeptides or polypeptide-containing nanoparticles indicated (0.1 to 1.0 mM). Contractile response was defined by stress, which was calculated using the force generated by the tissues. [$10^5$ Newtons (N)/$m^2$]=force (g)×0.0987/area, where area is equal to the wet weight [(mg)/length (mm at maximal length)] divided by 1.055). Percent relaxation were determined as a change to the maximal phenylephrine-induced contraction. Data are reported as mean responses±standard error of the mean. n=2-6.
Figure 7:
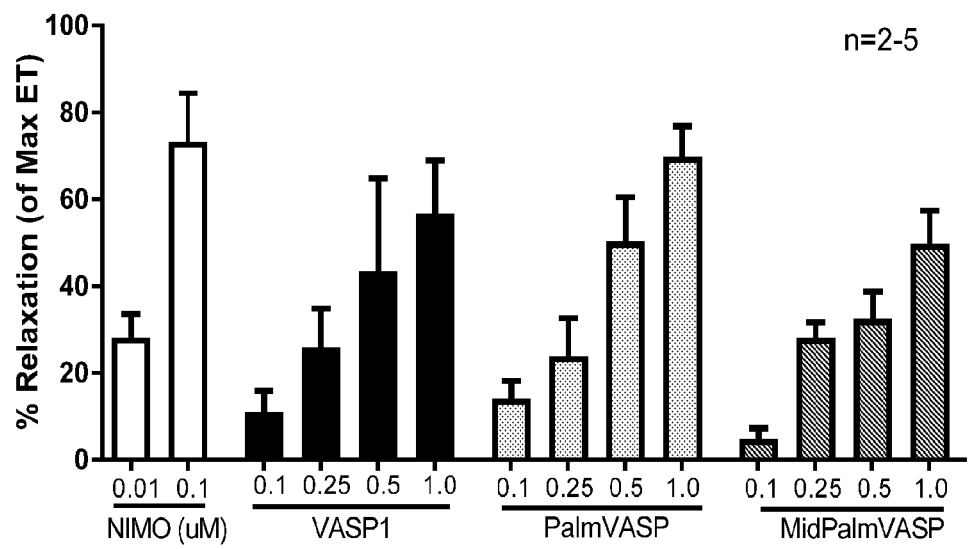
FIG. 7 shows a graph illustrating the effects of modified VASP on endothelin 1-precontracted rat aortic smooth muscle relaxation. Freshly isolated rat aorta denuded of endothelium were suspended in a muscle bath and force generated were recorded. Endothelin 1 (ET)-precontracted tissues were treated with either nimodipine (NIMO, 10 or 100 nM) or escalating doses of the polypeptides or polypeptide-containing nanoparticles indicated (0.1 to 1.0 mM). Contractile response was defined by stress, which was calculated using the force generated by the tissues. [$10^5$ Newtons (N)/$m^2$]=force (g)×0.0987/area, where area is equal to the wet weight [(mg)/length (mm at maximal length)] divided by 1.055). Percent relaxation were determined as a change to the maximal phenylephrine-induced contraction. Data are reported as mean responses±standard error of the mean. n=2-5.
Figure 8:
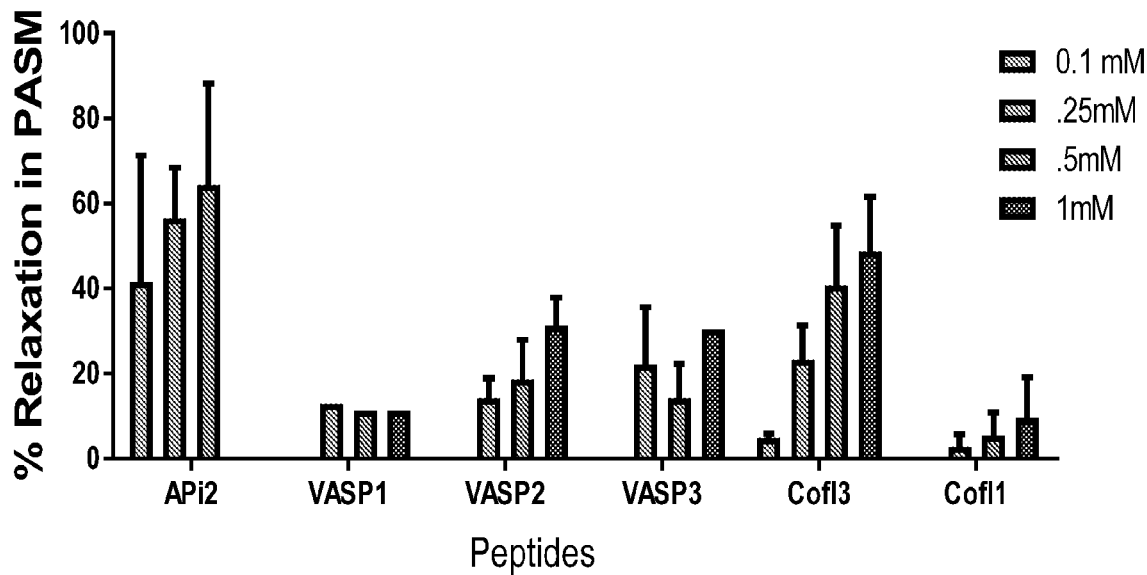
FIG. 8 shows a graph illustrating the effects of polypeptides on carbachol-induced contraction in airway smooth muscle. Bronchial rings were isolated from fresh porcine lung, suspended in a muscle bath, and force generated were recorded. Carbachol-precontracted tissues were treated with escalating doses of the polypeptides indicated (0.1 to 1.0 mM). Contractile response was defined by stress, which was calculated using the force generated by the tissues. [$10^5$ Newtons (N)/$m^2$]=force (g)×0.0987/area, where area is equal to the wet weight [(mg)/length (mm at maximal length)] divided by 1.055). Percent relaxation were determined as a change to the maximal carbachol-induced contraction. Data are reported as mean responses±standard error of the mean. n=2-4.

In some embodiments, the polypeptides disclosed herein have and/or provide smooth muscle relaxing properties. The signaling pathways that lead to smooth muscle relaxation include activation of the cyclic nucleotide signaling pathway guanylate cyclase/cGMP/cGMP-dependent protein kinase (PKG) and adenylate cyclase/cAMP/cAMP-dependent protein kinase (PKA and PKG). Activation of the PKA pathway leads to increases in the phosphorylation of the small heat shock protein, HSP20 which displaces cofilin from the docking protein 14-3-3. In one embodiment, one or more of the polypeptides include phosphopeptide analogues of cofilin (YARAAARQARAA(pS)GVAVSDG (SEQ ID NO: 1), YARAAARQARAA(pS)GVAVpSDG (SEQ ID NO: 2)) which directly cause smooth muscle relaxation (FIGS. 2 and 8). Additionally, increases in the phosphorylation of HSP27 inhibits smooth muscle relaxation and modulates actin polymerization. In another embodiment, one or more of the polypeptides include peptide analogues of HSP27 (YARAAARQARAIRQTADRWRVSLDVN (SEQ ID NO: 3), IRQTADRWRVSLDVNLTVK (SEQ ID NO: 4)) which directly cause smooth muscle relaxation (FIGS. 2 and 8). Furthermore, activation of the PKG pathway leads to increases in the phosphorylation of VASP (FIGS. 3A-B). In another embodiment, one or more of the polypeptides include phosphopeptide analogues of VASP (YARAAARQARAKLRKV(pS)K (SEQ ID NO: 5), YARAAARQARAKLRKVpSKQEEA (SEQ ID NO: 6), YARAAARQARAKLRV(pS)KQEEASG (SEQ ID NO: 7), KLRKV(pS)KLTVK (SEQ ID NO: 8)) which directly cause smooth muscle relaxation (FIGS. 2 and 8). SEQ ID NOs: 9 and 10 are control peptides that do not directly cause relaxation (FIG. 2). SEQ ID NOs: 11 and 12 are palmitization of SEQ ID NO: 5, which directly cause smooth muscle relaxation with enhanced potency (FIGS. 6 and 7).

Also provided herein are methods of synthesizing the polypeptides. In some embodiments, the polypeptides described herein are chemically synthesized or recombinantly expressed. Preferably, the polypeptides of the present invention are chemically synthesized. Synthetic polypeptides may be prepared using the well-known techniques of solid phase, liquid phase, or peptide condensation techniques, any other suitable technique, or any combination thereof. Solid phase peptide synthesis may be accomplished by techniques familiar to those in the art and provided, for example, in Stewart and Young, 1984, Solid Phase Synthesis, Second Edition, Pierce Chemical Co., Rockford, Ill.; Fields and Noble, 1990, Int. J. Pept. Protein Res. 35: 161-214, or using automated synthesizers.

The synthetic polypeptides may include natural and/or unnatural amino acids. Amino acids used for peptide synthesis may be standard Boc (N.alpha.-amino protected N.alpha.-t-butyloxycarbonyl) amino acid resin with the standard deprotecting, neutralization, coupling and wash protocols of the original solid phase procedure of Merrifield (1963, J. Am. Chem. Soc. 85: 2149-2154), or the base-labile N.alpha.-amino protected 9-fluorenylmethoxycarbonyl (Fmoc) amino acids first described by Carpino and Han (1972, J. Org. Chem. 37: 3403-3409). Both Fmoc and Bac N.alpha.-amino protected amino acids can be obtained from Sigma, Cambridge Research Biochemical, or other chemical companies familiar to those skilled in the art. In addition, the polypeptides can be synthesized with other N.alpha.-protecting groups that are familiar to those skilled in this art. Other synthetic amino acids include ornithine for lysine, and norleucine for leucine or isoleucine.

In embodiments where the S residue is phosphorylated, the peptide can be synthesized using a phosphorylated amino acid (or phospho-mimic) during polypeptide synthesis, or the S residue can be phosphorylated after its addition to the polypeptide chain.

In certain embodiments, the polypeptides disclosed herein may comprise D-amino acids (which are resistant to L-amino acid-specific proteases in vivo), a combination of D- and L-amino acids, and various "designer" amino acids (e.g., beta.-methyl amino acids, C.alpha.-methyl amino acids, and N.alpha.-methyl amino acids, etc.) to convey special properties. The special properties include, but are not limited to, anti-aggregation, increased stability, and/or increased potency.

Further provided herein are compositions including one or more of the polypeptides. In one embodiment, for example, the compositions include pharmaceutical compositions comprising at least one polypeptide according to one or more of the embodiments disclosed herein, modified based on formulatory and/or chemical approaches. Formulation modifications include, but are not limited to, polymeric nanoparticles, such as, but not limited to, the nanoparticles disclosed in U.S. patent application Ser. No. 14/784,017, which is hereby incorporated by reference in its entirety; lipidic nanoparticles; and/or drug-polymer conjugates. In some embodiments, the formulation modifications, such as the nanoparticles, increase potency and/or duration of the effect of the polypeptides. Chemical modifications include, but are not limited to, incorporation of non-natural amino acids, glycosylation, PEGylation, lipidation, and/or cyclization. Additionally or alternatively, the pharmaceutical compositions may include one or more of the polypeptides disclosed herein and a pharmaceutically acceptable carrier. Such pharmaceutical compositions are especially useful for carrying out the methods of the invention described below.

In some embodiments, the compositions include at least one calcium channel blocker and one or more of the polypeptides disclosed herein. In some embodiments, one or more of the polypeptides disclosed herein is modified with at least one molecule having one or more aromatic rings. In one embodiment, the one or more aromatic rings can be independently substituted with halogen, lower alkyl, lower alkylthio, trifluoromethyl, lower acyloxy, aryl, and heteroaryl. For example, in another embodiment, the at least one molecule includes 9-fluorenylmethyl (Fm). In another embodiment, the 9-fluorenylmethyl includes, but is not limited to, 9-fluorenylmethylcarbonyl, 9-fluorenylmethylcarbamates, 9-fluorenylmethylcarbonates, 9-fluorenylmethyl esters, 9-fluorenylmethylphosphates, S-9-fluorenylmethyl thioethers, or a combination thereof. In embodiments where the molecule comprising an aromatic ring is not an amino acid, the molecule may be attached to the polypeptide by methods known in the art, including but not limited to, standard Fmoc protection chemistry employed in peptide synthesis.

Still further provided herein are methods of using the polypeptides and/or compositions disclosed herein. In one embodiment, as discussed above, the polypeptides and/or compositions disclosed herein, including, but not limited to, the peptides according to SEQ ID NOs: 1-8 and 11-12, form a novel family of peptides that provide smooth muscle relaxation. In another embodiment, the polypeptides provide smooth muscle relaxation without or substantially without causing hypotension. In a further embodiment, the smooth muscle relaxation provided by the polypeptides and/or compositions disclosed herein facilitates proper and/or improved function of blood vessels, lung airways, uterus, intestine and bladder. In a further embodiment, the polypeptides and/or compositions disclosed herein form therapeutic agents for (a) promoting smooth muscle relaxation and preventing vasospasm; (b) neuroprotection (c) regulating actin polymerization; (d) platelet aggregation; and/or (e) treating or inhibiting one or more of subarachnoid induced vasospasm, intimal hyperplasia, stenosis, restenosis, atherosclerosis, smooth muscle spasm, angina, Prinzmetal's angina (coronary vasospasm), ischemia, stroke, hypertension, pulmonary (lung) hypertension, asthma (bronchospasm), Raynaud's disease or phenomenon, non-occlusive mesenteric ischemia, anal fissure, achalasia, sexual dysfunction, migraine, vasculopathy, such as transplant vasculopathy, stunned myocardium, pulmonary hypertension, and gastrointestinal motility disorders.

Accordingly, in some embodiments, a method of treating a condition includes administering the polypeptide and/or composition to a subject in need thereof. In one embodiment, the condition includes, but is not limited to, any condition involving vasospasm and/or unwanted smooth muscle contraction; any condition requiring neuroprotection; any condition involving unregulated actin polymerization; any condition requiring platelet aggregation; and/or one or more of subarachnoid induced vasospasm, intimal hyperplasia, stenosis, restenosis, atherosclerosis, smooth muscle spasm, angina, Prinzmetal's angina (coronary vasospasm), ischemia, stroke, hypertension, pulmonary (lung) hypertension, asthma (bronchospasm), Raynaud's disease or phenomenon, non-occlusive mesenteric ischemia, anal fissure, achalasia, sexual dysfunction, migraine, vasculopathy, such as transplant vasculopathy, stunned myocardium, pulmonary hypertension, and gastrointestinal motility disorders. In another embodiment, one or more of the polypeptides disclosed herein are phosphorylated. In a further embodiment, the method includes administering the polypeptide and/or composition where Z3 includes serine or phosphoserine analogs for the preparation of a medicament for carrying out one or more of the following therapeutic uses: (a) promoting smooth muscle relaxation and preventing vasospasm; (b) neuroprotection (c) regulating actin polymerization; (d) platelet aggregation; (e) treating or inhibiting one or more of subarachnoid induced vasospasm, intimal hyperplasia, stenosis, restenosis, atherosclerosis, smooth muscle spasm, angina, Prinzmetal's angina (coronary vasospasm), ischemia, stroke, hypertension, pulmonary (lung) hypertension, asthma (bronchospasm), Raynaud's disease or phenomenon, non-occlusive mesenteric ischemia, anal fissure, achalasia, sexual dysfunction, migraine, vasculopathy, such as transplant vasculopathy, stunned myocardium, pulmonary hypertension, and gastrointestinal motility disorders. In certain embodiments, the subject is a mammal, including, but not limited to, a human.

As used herein, "Pulmonary hypertension" means a disorder in which the blood pressure in the arteries supplying the lungs is abnormally high. Causes include, but are not limited to, inadequate supply of oxygen to the lungs, such as in chronic bronchitis and emphysema; pulmonary embolism, and intestinal pulmonary fibrosis. Symptoms and signs of pulmonary hypertension are often subtle and nonspecific. In the later stages, pulmonary hypertension leads to right heart failure that is associated with liver enlargement, enlargement of veins in the neck and generalized edema. Treating pulmonary hypertension includes one or more of the following (a) decreasing blood pressure in the arteries supplying the lungs to closer to normal levels for the individual, or closer to a desired pressure; (b) limiting or preventing the occurrence of one or more of enlargement of veins in the neck, enlargement of the liver, and generalized edema in patients suffering from pulmonary hypertension; (c) inhibiting worsening of one or more of enlargement of veins in the neck, enlargement of the liver, and generalized edema in patients suffering from pulmonary hypertension and its symptoms; (d) limiting or preventing recurrence of pulmonary hypertension in patients that previously suffered from pulmonary hypertension; and (e) limiting or preventing recurrence of one or more of enlargement of veins in the neck, enlargement of the liver, and generalized edema in patients that previously suffered from pulmonary hypertension. Similarly, methods to prevent pulmonary hypertension involve administration of the one or more polypeptides according to the present invention to a subject that suffers from one or more of chronic bronchitis, emphysema, pulmonary embolism, and intestinal pulmonary fibrosis.

As used herein, "Stunned myocardium" means heart muscle that is not functioning (pumping/beating) due to cardiac ischemia (lack of blood flow/oxygen to the vessels supplying the heat muscle). Treating stunned myocardium means one or more of (a) improving the ability of the heart muscle to pump by improving the oxygenation of the ischemic muscle, or by decreasing the need of the myocardial cells for oxygen and (b) limiting or preventing recurrence of stunned myocardium in patients that previously suffered from stunned myocardium. Preventing stunned myocardium involves administration of the one or more polypeptides according to the present invention to a subject that suffers from cardiac ischemia.

In various other embodiments disclosed herein, particularly those that involve inhibiting intimal hyperplasia, the method is performed on a subject who has undergone, is undergoing, or will undergo a procedure selected from the group consisting of angioplasty, vascular stent placement, endarterectomy, atherectomy, bypass surgery (such as coronary artery bypass surgery; peripheral vascular bypass surgeries), vascular grafting, organ transplant, prosthetic device implanting, microvascular reconstructions, plastic surgical flap construction, and catheter emplacement.

In a further embodiment, the methods of the invention are used for treating or preventing smooth muscle spasm, comprising contacting a subject or graft in need thereof with an amount effective to inhibit smooth muscle spasm of one or more polypeptides according to the invention. Smooth muscles are found in the walls of blood vessels, airways, the gastrointestinal tract, and the genitourinary tract. Pathologic tonic contraction of smooth muscle constitutes spasm. Many pathological conditions are associated with spasm of vascular smooth muscle ("vasospasm"), the smooth muscle that lines blood vessels. This can cause symptoms such as angina and ischemia (if a heart artery is involved), or stroke as in the case of subarachnoid hemorrhage-induced vasospasm if a brain vessel is involved. Hypertension (high blood pressure) is caused by excessive vasoconstriction, as well as thickening, of the vessel wall, particularly in the smaller vessels of the circulation.

It has been shown that VASP, and certain peptides derived therefrom, are effective at inhibiting smooth muscle spasm, such as vasospasm, and may exert their anti-smooth muscle spasm effect by promoting smooth muscle vasorelaxation and inhibiting contraction. Additionally, it has been shown that VASP deficiency increases blood-brain-barrier damage after ischemic stroke. More specifically, glutamate concentration increases after subarachnoid hemorrhage and correlates with subarachnoid hemorrhage induced vasospasm. Glutamate reduces VASP phosphorylation in brain endothelium and is associated with altered endothelial permeability.

Accordingly, in some embodiments, the method includes administering the polypeptides and/or compositions disclosed herein to treat or inhibit muscle cell spasms, such as vasospasms. Preferred embodiments of the method include, but are not limited to, methods to treat or inhibit angina, coronary vasospasm, Prinzmetal's angina (episodic focal spasm of an epicardial coronary artery), ischemia, stroke, bradycardia, and hypertension. In various other embodiments, the muscle cell spasm is associated with a disorder including, but not limited to pulmonary (lung) hypertension, asthma (bronchospasm), toxemia of pregnancy, pre-term labor and/or delivery, pre-eclampsia/eclampsia, Raynaud's disease or phenomenon, hemolytic-uremia, non-occlusive mesenteric ischemia (ischemia of the intestines that is caused by inadequate blood flow to the intestines), anal fissure (which is caused by persistent spasm of the internal anal sphincter), achalasia (which is caused by persistent spasm of the lower esophageal sphincter), digestive tract disorders (which can be caused by over active contractile mechanisms); male or female sexual dysfunction (which is caused by a lack of relaxation of the vessels in the penis or clitoris, as erection requires vasodilation of the corpra cavemosal (penile or vaginal) blood vessels); migraine (which is caused by spasm of the intracranial blood vessels), ischemic muscle injury associated with smooth muscle spasm, and vasculopathy, such as transplant vasculopathy (a reaction in the transplanted vessels which is similar to atherosclerosis, it involves constrictive remodeling and ultimately obliteration of the transplanted blood vessels, this is the leading cause of heart transplant failure).

In some embodiments, when calcium channel blockers are provided together with the polypeptides, the calcium channel blockers work in concert with the smooth muscle relaxing peptides to synergistically increase and/or enhance muscle relaxation, as illustrated in FIGS. 4A-B and 5A-B.

Without wishing to be bound by theory, this is believed to result from calcium channel blockers or inhibitors, such as nifedipine and nimodipine, providing an alternate pathway for relaxation of smooth muscles through decreases in intracellular calcium concentrations.

Additionally or alternatively, in certain embodiments, the polypeptides and/or compositions may be administered to a subject in need of treatment for conditions associated with platelet aggregation. Platelet aggregation or activation at the site of vascular injury leads to thrombus (clot) formation. Activation of platelets is inhibited by cAMP- and cGMP mediated signaling. VASP deficiency reduces inhibition of platelet activation and therefore plays an important role in platelet aggregation. While existing anti-platelet drugs lead to PKA activation and VASP phosphorylation in platelets, a large portion of patients do not respond adequately to such drugs. In contrast, the polypeptides and/or compositions disclosed herein provide increased prevention of platelet activation.

The presently-disclosed subject matter also includes improved biomedical devices, wherein the biomedical devices comprise one or more of the polypeptides and/or compositions disposed on or in the biomedical device. In one embodiment, the one or more polypeptides are phosphorylated, as discussed above. In another embodiment, biomedical devices include stents, grafts, shunts, stent grafts, angioplasty devices, balloon catheters, fistulas, wound dressings, any implantable drug delivery device, or a combination thereof.

In one embodiment, for example, the biomedical device includes a graft having one or more of the polypeptides and/or compositions disposed thereon and/or therein. In another embodiment, treatment of a graft, such as a vein or arterial graft, with the one or more polypeptides or compositions disclosed herein inhibits smooth muscle spasm. One of the ideal conduits for peripheral vascular and coronary reconstruction is the greater saphenous vein. However, the surgical manipulation during harvest of the conduit often leads to vasospasm. The exact etiology of vasospasm is complex and most likely multifactorial. Most investigations have suggested that vasospasm is either due to enhanced constriction or impaired relaxation of the vascular smooth muscle in the media of the vein. Numerous vasoconstricting agents such as endothelin-1 and thromboxane are increased during surgery and result in vascular smooth muscle contraction. Other vasoconstrictors such as norepinephrine, 5-hydroxytryptamine, acetylcholine, histamine, angiotensin II, and phenylephrine have been implicated in vein graft spasm. Papaverine is a smooth muscle vasodilator that has been used. In circumstances where spasm occurs even in the presence of papaverine, surgeons use intraluminal mechanical distension to break the spasm. This leads to injury to the vein graft wall and subsequent intimal hyperplasia.

Intimal hyperplasia is a complex process that leads to graft failure, and is the most common cause of failure of arterial bypass grafts. While incompletely understood, intimal hyperplasia is mediated by a sequence of events that include endothelial cell injury and subsequent vascular smooth muscle proliferation and migration from the media to the intima. This process is associated with a phenotypic modulation of the smooth muscle cells from a contractile to a synthetic phenotype. The "synthetic" smooth muscle cells secrete extracellular matrix proteins, which leads to pathologic narrowing of the vessel lumen leading to graft stenoses and ultimately graft failure. Such endothelial cell injury and subsequent smooth muscle cell proliferation and migration into the intima also characterize restenosis, most commonly after angioplasty to clear an obstructed blood vessel.

Thus, in some embodiments, the graft can be contacted with the one or more polypeptides and/or compositions disclosed herein, during harvest from the graft donor, subsequent to harvest (before implantation), and/or during implantation into the graft recipient (i.e., ex vitro or in vivo). This can be accomplished, for example, by delivering the recombinant expression vectors (most preferably a viral vector, such as an adenoviral vector) of the invention to the site, and transfecting the smooth muscle cells. More preferably, delivery into smooth muscle is accomplished by using the one or more polypeptides that include at least one transduction domain to facilitate entry into the smooth muscle cells. During graft implantation, it is preferred that the subject receiving be treated systemically with heparin, as heparin has been shown to bind to protein transduction domains and prevent them from transducing into cells. This approach will lead to localized protein transduction of the graft alone, and not into peripheral tissues. The methods of this embodiment inhibit vein graft spasm during harvest and/or implantation of the graft, and thus improve both short and long term graft success.

Still further provided herein are methods of administering the polypeptides according to one or more of the embodiments disclosed herein. For administration, the polypeptides are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, dextran sulfate, heparin-containing gels, and/or polyvinyl alcohol, and tableted or encapsulated for conventional administration. Alternatively, the compounds of this invention may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art. The polypeptides may be linked to other compounds to promote an increased half-life in vivo, such as polyethylene glycol. Such linkage can be covalent or non-covalent as is understood by those of skill in the art.

The polypeptides or pharmaceutical compositions thereof may be administered by any suitable route, including orally, parentarally, by inhalation spray, rectally, or topically in dosage unit formulations containing conventional pharmaceutically acceptable carriers, adjuvants, and vehicles. The term parenteral as used herein includes, subcutaneous, intravenous, intra-arterial, intramuscular, intrasternal, intratendinous, intraspinal, intracranial, intrathoracic, infusion techniques or intraperitoneally. Preferred embodiments for administration vary with respect to the condition being treated.

The polypeptides may be made up in a solid form (including granules, powders or suppositories) or in a liquid form (e.g., solutions, suspensions, or emulsions). The polypeptides of the invention may be applied in a variety of solutions. Suitable solutions for use in accordance with the invention are sterile, dissolve sufficient amounts of the polypeptides, and are not harmful for the proposed application.

Suitable routes of delivery for these various indications of the different embodiments of the methods of the invention vary. For example, in some embodiments, topical administration is preferred for methods involving treatment or inhibition of vein graft spasm, intimal hyperplasia, restenosis, prosthetic graft failure due to intimal hyperplasia, stent, stent graft failure due to intimal hyperplasia/constrictive remodeling, microvascular graft failure due to vasospasm, transplant vasculopathy, and male and female sexual dysfunction. As used herein, "topical administration" refers to delivering the polypeptide onto the surface of the organ.

Intrathecal administration, defined as delivering the polypeptide into the cerebrospinal fluid is the preferred route of delivery for treating or inhibiting stroke and subarachnoid hemorrhage induced vasospasm. Endovascular coiling is the preferred rouse of delivery for treating SAH. Intraperitoneal administration, defined as delivering the polypeptide into the peritoneal cavity, is the preferred route of delivery for treating or inhibiting non-occlusive mesenteric ischemia. Oral administration is the preferred route of delivery for treating or inhibiting achalasia. Intravenous administration is the preferred route of delivery for treating or inhibiting hypertension and bradycardia. Administration via suppository is preferred for treating or inhibiting anal fissure. Aerosol delivery is preferred for treating or inhibiting asthma (ie: bronchospasm). Intrauterine administration is preferred for treating or inhibiting pre-term labor and/or delivery, pre-eclampsia/eclampsia, and intrauterine growth restriction.

In some embodiments of the methods disclosed herein, such as promoting smooth muscle relaxation, the administering may be direct, by contacting a blood vessel in a subject being treated with one or more polypeptides of the invention. For example, a liquid preparation of one or more polypeptides according to the invention can be forced through a porous catheter, or otherwise injected through a catheter to the injured site, or a gel or viscous liquid containing the one or more polypeptides according to the invention can be spread on the injured site. In these embodiment of direct delivery, it is most preferred that the one or more polypeptides according to the invention be delivered into smooth muscle cells at the site of injury or intervention. More preferably, delivery into smooth muscle cells is accomplished by using the one or more polypeptides according to the invention that include at least one transduction domain to facilitate entry into the smooth muscle cells.

As used herein for all of the methods of the invention, an "amount effective" of the one or more polypeptides is an amount that is sufficient to provide the intended benefit of treatment. An effective amount of the polypeptides that can be employed ranges generally between about 0.01 .mu.g/kg body weight and about 10 mg/kg body weight, preferably ranging between about 0.05 .mu.g/kg and about 5 mg/kg body weight. However dosage levels are based on a variety of factors, including the type of injury, the age, weight, sex, medical condition of the individual, the severity of the condition, the route of administration, and the particular compound employed. Thus, the dosage regimen may vary widely, but can be determined routinely by a physician using standard methods.

The presently-disclosed subject matter may be better understood with reference to the accompanying examples that are intended for purposes of illustration only and should not be construed to limit the scope of the invention.

EXAMPLES

Example 1

This example illustrates a study of vasorelaxation of rat aorta to polypeptides. Rat aortic rings, denuded of the endothelium, were suspended in a muscle bath containing bicarbonate buffer (120 mM NaCl, 4.7 mM KCl, 1.0 mM $MgSO_4$, 1.0 mM $NaH_2PO_4$, 10 mM glucose, 1.5 mM $CaCl_2$, and 25 mM $Na_2HCO_3$, pH 7.4), equilibrated with about 95% $O_2$-about 5% $CO_2$, at 37° C. at one gram of tension for 2 hours. The muscles were pre-contracted with the agonist phenylephrine (10-50 nM) and cumulative doses of the polypeptides. The result of this Experiment is illustrated in FIG. 2. Transduction with the peptide analogues of cofilin, Hsp27 and VASP caused a dose-dependent relaxation of rat aortic smooth muscle, with the exception of scrVASP1 (SEQ ID NO: 9 and SEQ ID NO: 10). This experiment also demonstrates X1 or X3 is required for the transduction of polypeptides into rat aorta. This experiment also demonstrates vasorelaxation caused by the VASP1 is sequence specific.

Example 2

This example illustrates the association of VASP protein phosphorylation to vasorelaxation. Human saphenous veins were suspended in the muscle bath. Tissues were treated left untreated (Basal), or contracted with phenylephrine (50 nM) for 5 min and relaxed with sodium nitroprusside (100 nM) for 3 min or nimodipine (1 µM) for 2 min. Tissues were snap-frozen under tension. Proteins were extracted, separated on a SDS-polyacrylamide gels, and transferred onto a nitrocellulose membrane. Level of VASP phosphorylation were detected using phosphorylation state-specific antibodies against VASP. The result of this study are illustrated in FIGS. 3A-B. The experiment demonstrates that relaxation of rat aorta is associated with increases in VASP phosphorylation. From this, the instant inventors surprisingly discovered that

Example 3

This experiment demonstrates that the VASP1 polypeptide works in concert with calcium channel blocker, nimodipine, to enhance vasorelaxation in ascular smooth muscle. Endothelium denuded rat aortic rings were suspended in the muscle bath. Phenylephrine or endothelin-1 pre-contracted tissues were treated with sodium nitroprusside, nimodipine, the VASP1 polypeptide (SEQ ID NO: 5), or a combination of nimodipine and the VASP1 polypeptide. The result of this Experiment is illustrated in FIGS. 4A-5B.

Example 4

Figure 5A:
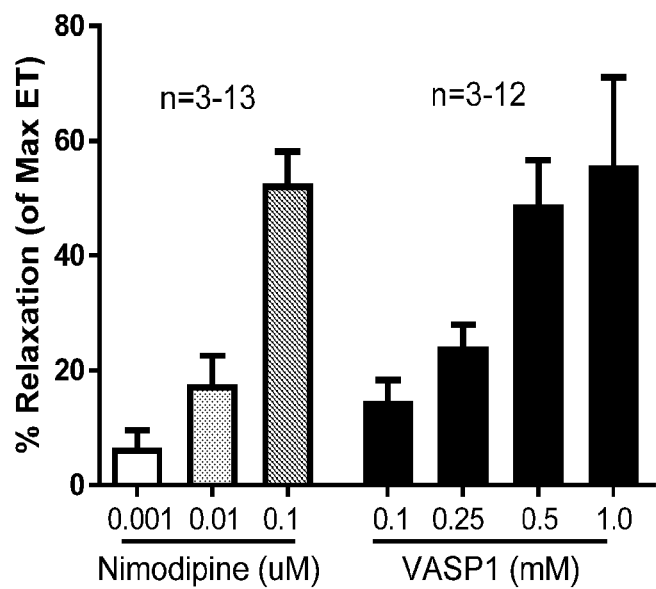
FIGS. 5A-B shows graphs illustrating the effects of nimodipine on polypeptide induced vasorelaxation in endothelin-1 precontracted rat aortic smooth muscle. Freshly isolated rat aorta denuded of endothelium were suspended in a muscle bath and force generated were recorded. (A) Endothelin 1 (ET)-precontracted tissues were treated either with escalating doses of the calcium channel blocker nimodipine (NIMO; 0.001 to 0.1 uM), the VASP1 polypeptide (0.1 to 1.0 mM). (B) ET-precontracted tissues were treated with VASP1 polypeptide alone (0.25 mM), nimodipine alone (0.01 or 0.1 uM), nimodipine (0.01 or 0.1 uM) followed by the VASP1 polypeptide (0.25 mM), [NIMO/VASP1], the VASP1 polypeptide (0.25 mM) followed by nimodipine (0.01 or 0.1 uM), [VASP1/NIMO], or simultaneous addition of nimodipine (0.1 uM) plus the VASP1 polypeptide (0.25 mM) [NIMO+VASP1]. Contractile response was defined by stress, which was calculated using the force generated by the tissues. [$10^5$ Newtons (N)/$m^2$]=force (g)×0.0987/area, where area is equal to the wet weight [(mg)/length (mm at maximal length)] divided by 1.055). (A) Percent relaxation were determined as a change to the maximal phenylephrine-induced contraction. Data are reported as mean responses±standard error of the mean. n=2-12.
Figure 5B:
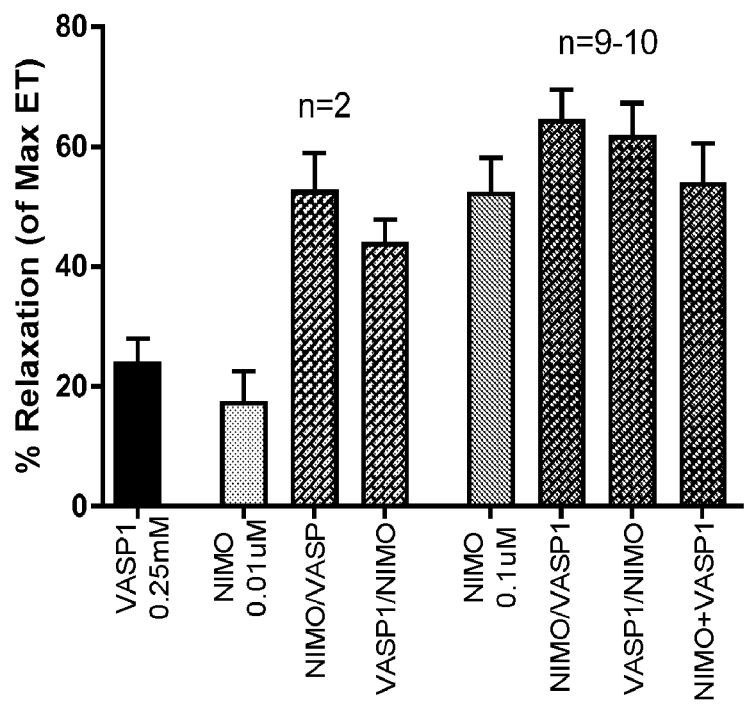

This experiment shows the relaxation of airway smooth muscle induced by the polypeptides. Bronchial rings were suspended in the muscle bath and equilibrated for 3 hours at a basal tension of 1 gram. Rings were then contracted with the agonist carbachol (150 nM) and then relaxed with cumulative doses of the polypeptides (0.1 to 1.0 mM). The result of this examples is illustrated in FIGS. 5A-B. The experiment shows that airway smooth muscle is relaxed with peptide homologues of cofilin, Hsp27, and VASP.

Example 5

This experiment demonstrates that potency of the VASP1 polypeptide in vasorelaxation can be enhanced by chemical or formulatory modification. The VASP1 polypeptide was conjugated to palmitic acid (SEQ ID NOs: 11 and 12) or complexed with polyacrylic acid to form nanoparticles. Endothelium denuded rat aortic rings were in the muscle bath. Phenylephrine or endothelin-1 pre-contracted tissues were treated with sodium nitroprusside, nimodipine, the VASP1 polypeptide (SEQ ID NOs: 5, 11, and 12) or VASP1 polypeptide containing nanoparticle. The results of this experiment are illustrated in FIGS. 6-7.

Example 6

Figure 9:
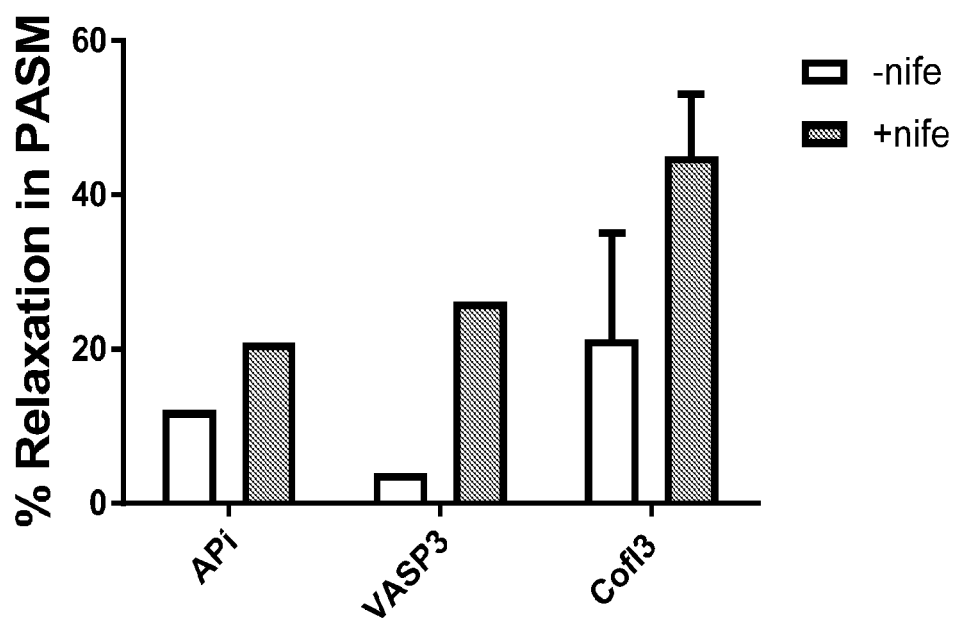
FIG. 9 shows a graph illustrating the effects of nifedipine on polypeptide-induced relaxation in carbachol precontracted airway smooth muscle. Freshly isolated porcine bronchial rings were suspended in a muscle bath. Carbachol-precontracted tissues were treated with the polypeptides alone (−nife) or 0.1 uM nifedipine followed by the polypeptides (+nife). Contractile response was defined by stress, which was calculated using the force generated by the tissues. [$10^5$ Newtons (N)/$m^2$]=force (g)×0.0987/area, where area is equal to the wet weight [(mg)/length (mm at maximal length)] divided by 1.055). Percent relaxation were determined as a change to the maximal carbachol-induced contraction. Data are reported as mean responses±standard error of the mean. n=1-2.

This study shows that calcium channel blockers work in concert with polypeptides in airway smooth muscle. Porcine bronchial rings were suspended in the muscle bath. Tissues were treated with channel blocker alone, polypeptide alone, or in combination. The results of these study are illustrated in FIG. 9.

Results for Examples 1-6

Taken together, these data suggest that short sequences or motifs surrounding a phosphorylation site can have profound effects on smooth muscle function. These data also suggest that short sequence or motif surrounding actin binding site can have effects on smooth muscle function.

The transduction of peptide motifs that modulate smooth muscle relaxation provides a framework for the development of peptide-based therapeutics. One of the advantages of this approach is the evolutionary specificity of downstream protein targets. Receptor based modulation of signaling cascades leads to amplifying enzymatic activities. Thus, exploiting specific post-translational modifications of proteomic targets is potentially more stoichiometric and thus suitable for finer regulation of cellular processes. This approach also has advantages over gene therapy in that there are no delays in protein production or difficulties with regulating the amount of protein expression. Finally, this approach may be feasible for the treatment of specific modalities that are refractory to activation of upstream receptors or signaling cascades. For example, the vasospasm associated with subarachnoid hemorrhage occurs coincident with downregulation of the expression of NO, cGMP, guanylate cyclase, PKG, and VASP. These peptide analogues could be exploited for the treatment of intracerebral vasospasm.

Materials and Methods

Tissue Procurement

Rat aortae were isolated from euthanized female Sprague-Dawley rats. Porcine bronchial rings were isolated from lung obtained from euthanized female Yorkshire pigs.

Peptide Synthesis and Purification

Peptides were synthesized using standard f-moc chemistry and purified using high performance liquid chromatography (HPLC) by EZ Biolabs (Carmel, Ind.).

Immunoblotting

Tissues were snap-frozen under tension and homogenized. Proteins were extracted using a lysis buffer (150 mM NaCl, 50 mM pH8, 1% NP-40, 0.5% Na Deoxycholate, 5 mM EDTA, 5 mM EGTA supplemented with protease and phosphatase inhibitors). Proteins from tissue lysate (30 ug) were separated on 8% SDS-PAGE gels and transferred to nitrocellulose membrane (LI-COR, Lincoln, Nebr.). The blots were blocked in LI-COR blocking buffer for 1 hour. The blots were then incubated with either anti-VASP (1:1000, Cell Signaling, CA) or phosphorylation state-specific VASP antibody (1:1000, Cell Signaling) in LI-COR buffer/TBST for 16-18 hour at 4 C. The blots were washed 3 times (10 minutes each) in TBS/Tween-20. The blots were then incubated with donkey anti-rabbit or donkey anti-goat secondary antibody (LI-COR) diluted in LI-COR buffer/TBST (1:20,000) for 1 hour at room temperature. The blots were then washed 3 times (10 minutes each) in TBS/Tween-20. Immunoreactive protein was detected using near infrared fluorescent imager (LI-COR).

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A polypeptide comprising:
an amino acid sequence according to the general formula X1-X2-X3;
wherein one of X1 and X3 comprises a first transduction domain, and the other is absent or comprises a second transduction domain;
wherein X2 is selected from the group consisting of IRQTADRWRVSLDVN (SEQ ID NO: 34), A(pS)GVAVSDG (SEQ ID NO: 35), A(pS)GVTVSDEVI (SEQ ID NO: 36), KLRKV(pS)K (SEQ ID NO: 37), KLRKV(pS)KQEEA (SEQ ID NO: 38), KLRKV(pS)KQEEASG (SEQ ID NO: 39), KLRV(pS)K (SEQ ID NO: 40), K(pS)RVLKK (SEQ ID NO: 41), {K(palm)}LRKV(pS)K (SEQ ID NO: 42), {K(palm)}GGKLRKV(pS)K (SEQ ID NO: 43), and combinations thereof; and
wherein pS is a phosphoserine analog and {K(palm)} denotes a palmitic acid conjugated lysine.

2. The polypeptide of claim 1, wherein the polypeptide is a smooth muscle relaxing polypeptide.

3. The polypeptide of claim 1, wherein X1 and X3 are selected from the group consisting of GRKKRRQRRRPPQ (SEQ ID NO: 13), AYARAAARQARA (SEQ ID NO: 14), DAATATRGRSAASRPTERPRAPARSASRPRRPVE (SEQ ID NO: 15), GWTLNSAGYLLGLINLKALAALAK-KIL (SEQ ID NO: 16), PLSSISRIGDP (SEQ ID NO: 17), AAVALLPAVLLALLAP (SEQ ID NO: 18), AAVLLPVL-LAAP (SEQ ID NO: 19), VTVLALGALAGVGVG (SEQ ID NO: 20), GALFLGWLGAAGSTMGAWSQP (SEQ ID NO: 21), GWTLNSAGYLLGLINLKALAALAKKIL (SEQ ID NO: 22), KLALKLALKALKAALKLA (SEQ ID NO: 23), KETWWETWWTEWSQPKKKRKV (SEQ ID NO: 24), KAFAKLAARLYRKAGC (SEQ ID NO: 25), KAFAK-LAARLYRAAGC (SEQ ID NO: 26), AAFAKLAAR-LYRKAGC (SEQ ID NO: 27), KAFAALAARLYRKAGC (SEQ ID NO: 28), KAFAKLAAQLYRKAGC (SEQ ID NO: 29), AGGGGYGRKKRRQRRR (SEQ ID NO: 30), YGRKKRRQRRR (SEQ ID NO: 31), YARAAARQARA (SEQ ID NO: 32), LTVK (SEQ ID NO: 33), and combinations thereof.

4. The polypeptide of claim 1, wherein the polypeptide includes a sequence selected from the group consisting of YARAAARQARAA(pS)GVAVSDG (SEQ ID NO: 1), YARAAARQARAA(pS)GVTVSDEVI (SEQ ID NO: 2), YARAAARQARAIRQTADRWRVSLDVN (SEQ ID NO: 3), IRQTADRWRVSLDVNLTVK (SEQ ID NO: 4), YARAAARQARAKLRKV(pS)K (SEQ ID NO: 5), YARAAARQARAKLRKV(pS)KQEEA (SEQ ID NO: 6), YARAAARQARAKLRKV(pS)KQEEASG (SEQ ID NO: 7), KLRKV(pS)KLTVK (SEQ ID NO: 8), YARAAARQARA{K(palm)}LRKV(pS)K (SEQ ID NO: 11), YARAAARQARA{K(palm)}GGKLRKV(pS)K (SEQ ID NO: 12), and combinations thereof; wherein (pS) denotes a phosphoserine analog and {K(palm)} denotes palmitic acid conjugated lysine.

5. The polypeptide of claim 1, further comprising one or more mimics of a phosphorylated amino acid residue.

6. The polypeptide of claim 5, wherein the amino acid residue is selected from the group consisting of D, E, and combinations thereof.

7. The polypeptide of claim 1, wherein the polypeptide includes one or more formulation modifications.

8. The polypeptide of claim 7, wherein the one or more formulation modifications are selected from the group consisting of polymeric nanoparticles, lipidic nanoparticles, drug-polymer conjugates, and combinations thereof.

9. The polypeptide of claim 1, wherein the polypeptide includes one or more chemical modifications.

10. The polypeptide of claim 9, wherein the chemical modifications are selected from the group consisting of incorporation of non-natural amino acids, glycosylation, PEGylation, lipidation, cyclization, and combinations thereof.

11. The polypeptide of claim 1, wherein the polypeptide is modified with at least one molecule having one or more aromatic rings.

12. The polypeptide of claim 11, wherein the one or more aromatic rings are independently substituted with at least one substituent selected from the group consisting of halogen, lower alkyl, lower alkylthio, trifluoromethyl, lower acyloxy, aryl, heteroaryl, and combinations thereof.

13. The polypeptide of claim 12, wherein the at least one molecule includes 9-fluorenylmethyl.

14. The polypeptide of claim 13, wherein the at least one molecule is selected from the group consisting of 9-fluorenylmethylcarbonyl, 9-fluorenylmethylcarbamates, 9-fluorenylmethylcarbonates, 9-fluorenylmethyl esters, 9-fluorenylmethylphosphates, S-9-fluorenylmethyl thioethers, and a combination thereof.

15. A pharmaceutical composition comprising:
   a polypeptide according to claim 1; and
   one or more components selected from the group consisting of a pharmaceutically acceptable carrier, a calcium channel blocker, and a combination thereof.

16. The composition of claim 15, wherein the calcium block is selected from the group consisting of nifedipine and nimodipine.

17. A method of promoting smooth muscle relaxation or treating vasospasm, the method comprising administering the polypeptide of claim 1 to a subject in need thereof.

* * * * *